United States Patent
Schings et al.

(10) Patent No.: US 10,905,419 B2
(45) Date of Patent: Feb. 2, 2021

(54) CLOSURE ASSEMBLY FOR LINEAR SURGICAL STAPLER

(71) Applicant: ETHICON LLC, Guaynabo, PR (US)

(72) Inventors: Brian D. Schings, Cincinnati, OH (US); Jason Jones, Cincinnati, OH (US); Gregory J. Bakos, Mason, OH (US)

(73) Assignee: Ethicon LLC, Guaynabo, PR (US)

( * ) Notice: Subject to any disclaimer, the term of this patent is extended or adjusted under 35 U.S.C. 154(b) by 286 days.

(21) Appl. No.: 16/157,605

(22) Filed: Oct. 11, 2018

(65) Prior Publication Data
US 2020/0113562 A1 Apr. 16, 2020

(51) Int. Cl.
| | | |
|---|---|---|
| *A61B 17/072* | (2006.01) | |
| *A61B 17/11* | (2006.01) | |
| *A61B 17/115* | (2006.01) | |
| *A61B 17/00* | (2006.01) | |

(52) U.S. Cl.
CPC .......... *A61B 17/072* (2013.01); *A61B 17/115* (2013.01); *A61B 17/1114* (2013.01); *A61B 2017/00367* (2013.01); *A61B 2017/00477* (2013.01); *A61B 2017/0725* (2013.01); *A61B 2017/07264* (2013.01); *A61B 2017/07271* (2013.01); *A61B 2017/07278* (2013.01); *A61B 2017/07285* (2013.01)

(58) Field of Classification Search
CPC .......... A61B 2017/00367; A61B 2017/00477; A61B 2017/0725; A61B 2017/2946
See application file for complete search history.

(56) References Cited

U.S. PATENT DOCUMENTS

| | | |
|---|---|---|
| 4,892,244 A | 1/1990 | Fox et al. |
| 4,991,764 A | 2/1991 | Mericle |
| 5,141,144 A | 8/1992 | Foslien |
| (Continued) | | |

FOREIGN PATENT DOCUMENTS

| | | |
|---|---|---|
| EP | 0061466 A1 | 10/1982 |
| EP | 0178941 B1 | 4/1986 |
| (Continued) | | |

OTHER PUBLICATIONS

U.S. Appl. No. 15/889,363, entitled "Release Mechanism for Linear Surgical Stapler," filed Feb. 6, 2018.

(Continued)

*Primary Examiner* — Michelle Lopez
(74) *Attorney, Agent, or Firm* — Frost Brown Todd LLC

(57) ABSTRACT

A surgical stapler includes a first elongate member having a distal portion that supports a plurality of staple-forming pockets, a second elongate member having a distal portion that supports a staple cartridge, and a clamp member movable from an open position to a closed position to releasably clamp the first and second elongate members together. A clamp lockout feature is supported by the first elongate member and is moveable between a lockout position in which the clamp lockout feature prevents closure of the clamp member, and a release position in which the clamp lockout feature permits closure of the clamp member. An actuating feature is supported by the second elongate member and is configured to actuate the clamp lockout feature from the lockout position to the release position in response to approximation of the distal portions of the first and second elongate members.

20 Claims, 16 Drawing Sheets

(56) References Cited

U.S. PATENT DOCUMENTS

| | | |
|---|---|---|
| 5,636,779 A | 6/1997 | Palmer |
| 5,718,359 A | 2/1998 | Palmer et al. |
| 5,792,135 A | 8/1998 | Madhani et al. |
| 5,817,084 A | 10/1998 | Jensen |
| 5,878,193 A | 3/1999 | Wang et al. |
| 6,231,565 B1 | 5/2001 | Tovey et al. |
| 6,364,888 B1 | 4/2002 | Niemeyer et al. |
| 6,783,524 B2 | 8/2004 | Anderson et al. |
| 7,524,320 B2 | 4/2009 | Tierney et al. |
| 7,691,098 B2 | 4/2010 | Wallace et al. |
| 7,806,891 B2 | 10/2010 | Nowlin et al. |
| 7,905,381 B2 | 3/2011 | Baxter, III et al. |
| 7,954,686 B2 | 6/2011 | Baxter, III et al. |
| 8,348,129 B2 | 1/2013 | Bedi et al. |
| 8,479,969 B2 | 7/2013 | Shelton, IV |
| 8,523,041 B2 | 9/2013 | Ishitsuki et al. |
| 8,573,461 B2 | 11/2013 | Shelton, IV et al. |
| 8,573,465 B2 | 11/2013 | Shelton, IV |
| 8,602,288 B2 | 12/2013 | Shelton, IV et al. |
| 8,616,431 B2 | 12/2013 | Timm et al. |
| 8,783,541 B2 | 7/2014 | Shelton, IV et al. |
| 8,789,740 B2 | 7/2014 | Baxter, III et al. |
| 8,800,838 B2 | 8/2014 | Shelton, IV |
| 8,820,605 B2 | 9/2014 | Shelton, IV |
| 8,844,789 B2 | 9/2014 | Shelton, IV et al. |
| 9,155,537 B2 | 10/2015 | Katre et al. |
| 9,301,759 B2 | 4/2016 | Spivey et al. |
| 9,402,629 B2 | 8/2016 | Ehrenfels et al. |
| 9,539,007 B2 | 1/2017 | Dhakad et al. |
| 9,724,095 B2 | 8/2017 | Gupta et al. |
| 2009/0308907 A1 | 12/2009 | Nalagatla et al. |
| 2015/0018875 A1 | 1/2015 | Knodel |
| 2015/0034695 A1 | 2/2015 | Kapadia |
| 2015/0327855 A1 | 11/2015 | Katre |
| 2016/0135811 A1 | 5/2016 | Gupta et al. |
| 2016/0249920 A1 | 9/2016 | Gupta et al. |
| 2016/0262756 A1 | 9/2016 | Patankar et al. |
| 2016/0310136 A1 | 10/2016 | Gupta et al. |
| 2016/0338701 A1 | 11/2016 | Patankar et al. |
| 2016/0338702 A1 | 11/2016 | Ehrenfels et al. |
| 2017/0079652 A1 | 3/2017 | Dhakad et al. |
| 2017/0143335 A1 | 5/2017 | Gupta et al. |
| 2017/0143336 A1 | 5/2017 | Shah et al. |
| 2017/0325811 A1 | 11/2017 | Gupta et al. |

FOREIGN PATENT DOCUMENTS

| | | |
|---|---|---|
| EP | 0677273 B1 | 10/1995 |
| EP | 1702567 B1 | 9/2006 |
| EP | 2532312 B1 | 12/2012 |
| EP | 3065649 A1 | 9/2016 |
| EP | 2741685 B1 | 1/2017 |
| EP | 3155988 A1 | 4/2017 |
| EP | 2804541 B1 | 10/2017 |
| EP | 3 289 985 A1 | 3/2018 |
| EP | 3 520 713 A1 | 8/2019 |
| WO | WO 92/10976 A1 | 7/1992 |
| WO | WO 2017/056028 A1 | 4/2017 |
| WO | WO 2018/044669 A1 | 3/2018 |

OTHER PUBLICATIONS

U.S. Appl. No. 15/889,370, entitled "Lockout Assembly for Linear Surgical Stapler," filed Feb. 6, 2018.

U.S. Appl. No. 15/889,374, entitled "Features to Align and Close Linear Surgical Stapler," filed Feb. 6, 2018.

U.S. Appl. No. 15/889,376, entitled "Releasable Coupling Features for Proximal Portions of Linear Surgical Stapler," filed Feb. 6, 2018.

U.S. Appl. No. 15/889,388, entitled "Firing Lever Assembly for Linear Surgical Stapler," filed Feb. 6, 2018.

U.S. Appl. No. 15/889,390, entitled "Clamping Mechanism for Linear Surgical Stapler," filed Feb. 6, 2018.

U.S. Appl. No. 16/102,164, entitled "Firing System for Linear Surgical Stapler," filed Aug. 13, 2018.

U.S. Appl. No. 16/102,170, entitled "Clamping Assembly for Linear Surgical Stapler," filed Aug. 13, 2018.

U.S. Appl. No. 16/157,599, entitled "Anvil Assembly for Linear Surgical Stapler," filed Oct. 11, 2018.

U.S. Appl. No. 16/165,587, entitled "Decoupling Mechanism for Linear Surgical Stapler," filed Oct. 19, 2018.

European Search Report, Partial, and Provisional Written Opinion dated Dec. 20, 2019 for Application No. EP 19202804.1, 10 pgs.

European Search Report, Extended, and Written Opinion dated Mar. 30, 2020 for Application No. EP 19202804.1, 10 pgs.

International Search Report and Written Opinion dated Mar. 5, 2020 for Application No. PCT/IB2019/058689, 14 pgs.

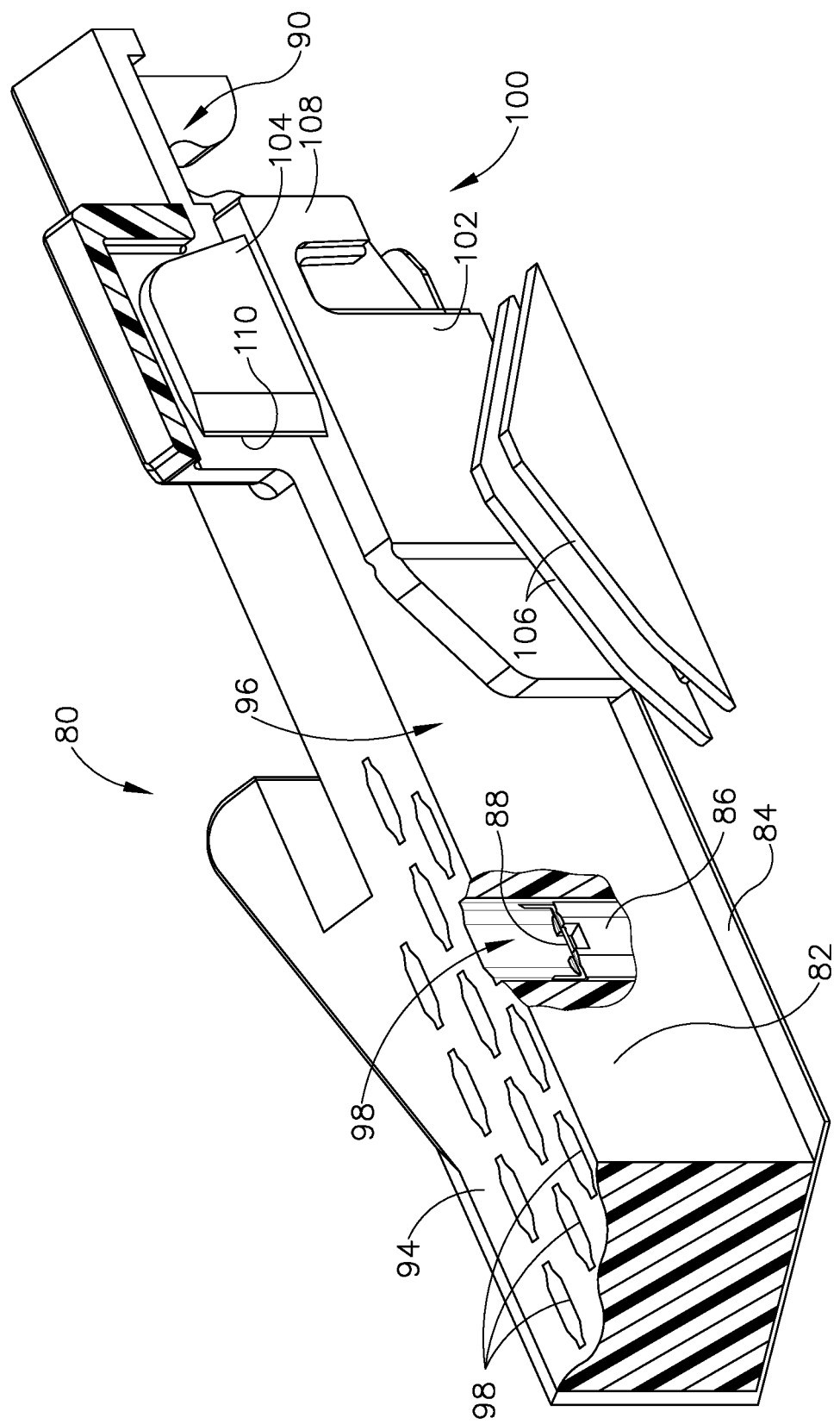

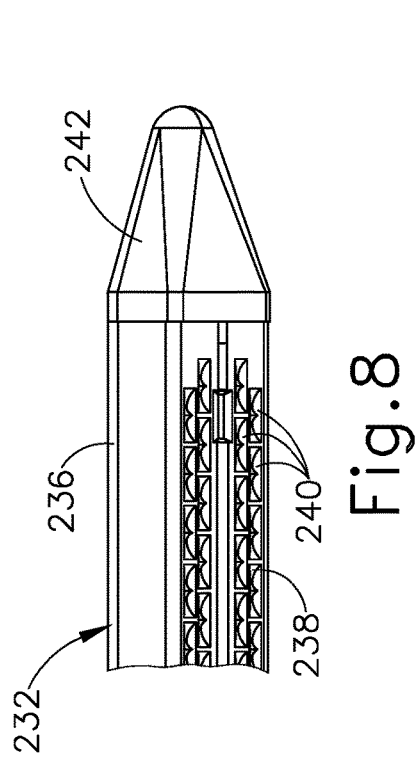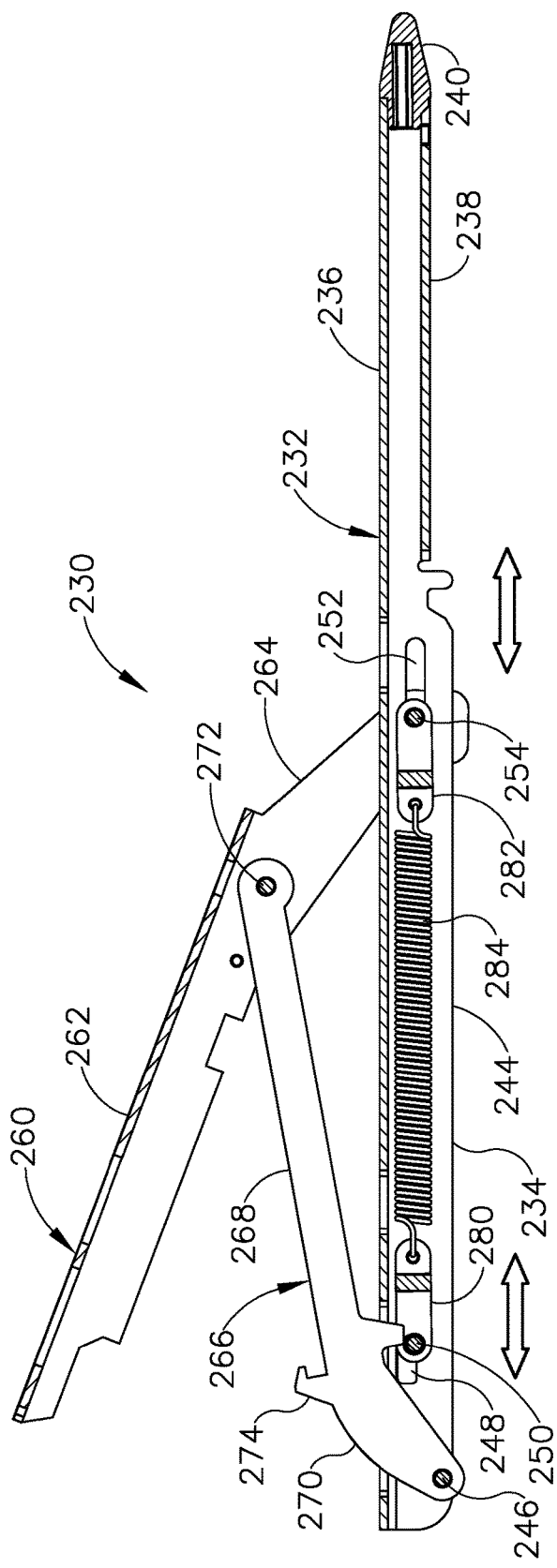

CLOSURE ASSEMBLY FOR LINEAR SURGICAL STAPLER

BACKGROUND

In some surgical operations, such as a gastrointestinal anastomosis, it may be desirable to clamp down on one or more layers of tissue, cut through the clamped layers, and simultaneously drive staples through the layers to substantially seal the severed layers of tissue together near their severed ends. One such instrument that may be used in such operations is a linear surgical stapler, also referred to as a "linear cutter." A linear surgical stapler generally includes a first half (referred to as a "cartridge half" or "reload half") having a distal jaw configured to support a staple cartridge (or "reload"), and a second half (referred to as an "anvil half") having a distal jaw that supports an anvil surface having staple-forming features. The stapler further includes a moveable clamp lever configured to releasably clamp the stapler halves together. The stapler halves are configured to pivot relative to one another to receive and clamp tissue between the two distal jaws when the clamp lever is closed. A firing assembly of the stapler is configured to be actuated to cut the clamped layers and simultaneously drive staples through the tissue on either side of the cut line. After firing the stapler, the clamp lever may be opened and the stapler halves separated to release the severed and stapled tissue.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 3 depicts a cross-sectional perspective view of a staple cartridge assembly of the linear surgical stapler of FIG. 1;

FIG. 8 depicts a perspective view of a distal end of an anvil half of the linear surgical stapler of FIG. 6;

FIG. 9 depicts a side cross-sectional view of the anvil half of the linear surgical stapler of FIG. 6;

Figure 1:
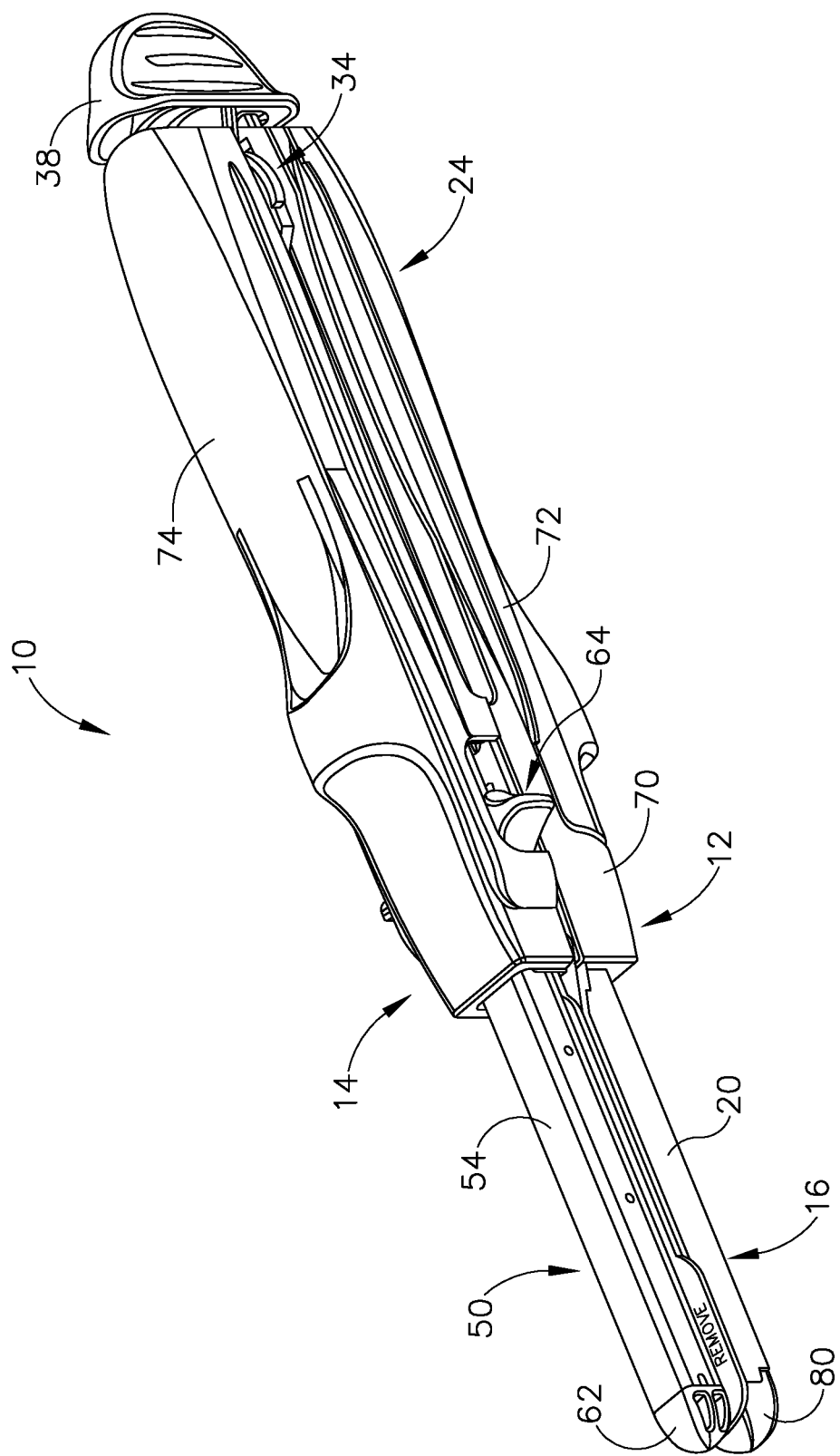
FIG. 1 depicts a distal perspective view of an exemplary linear surgical stapler, showing a cartridge half and an anvil half of the stapler coupled together with a clamp lever of the cartridge half in a fully closed position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the terms "about" and "approximately" for any numerical values or ranges indicate a suitable dimensional tolerance that allows the part or collection of components to function for its intended purpose as described herein.

I. Exemplary Linear Surgical Stapler

A. Overview of Linear Surgical Stapler

Figure 2:
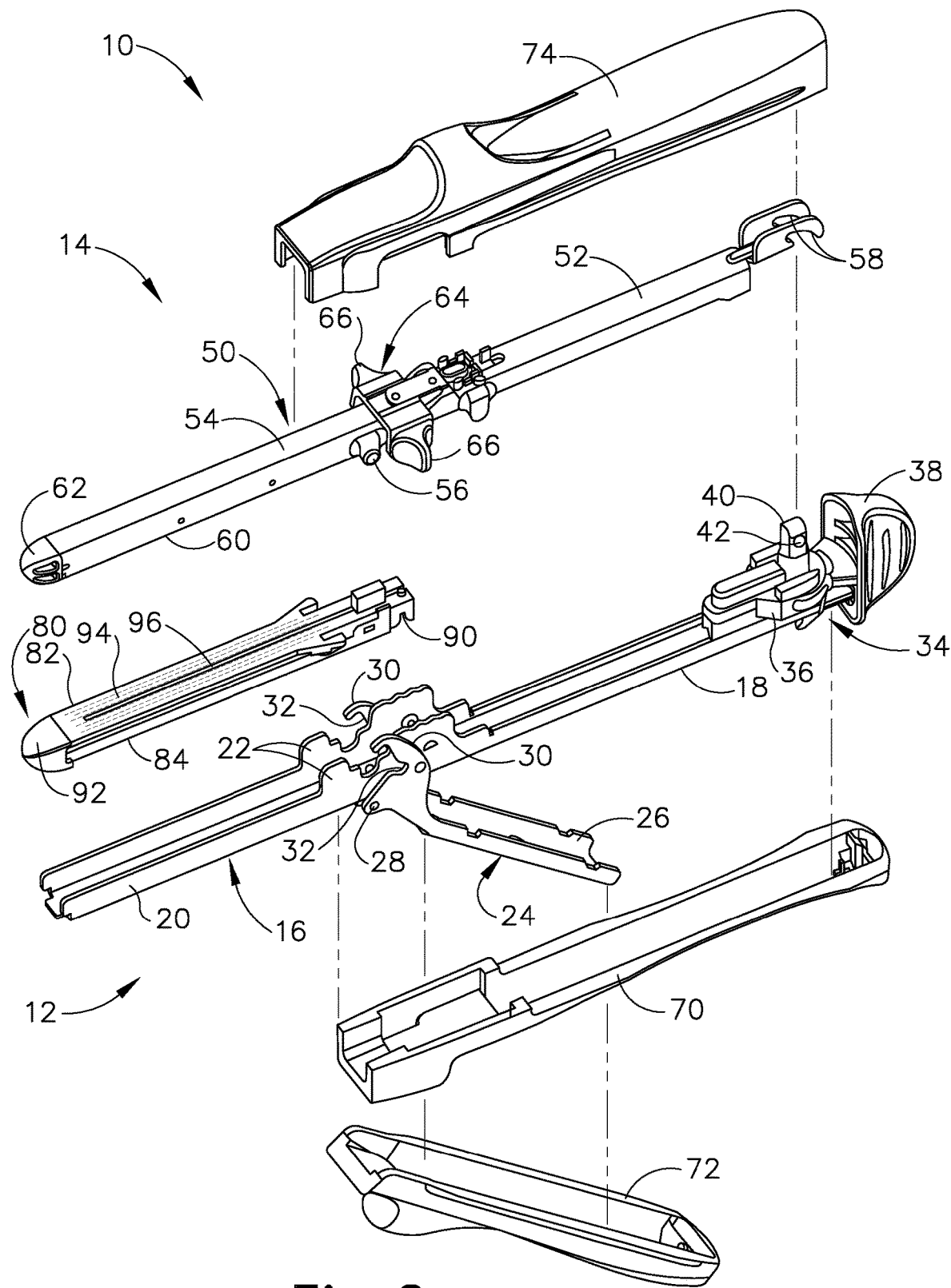
FIG. 2 depicts an exploded perspective view of the linear surgical stapler of FIG. 1.

FIGS. 1 and 2 show an exemplary linear surgical stapler (10) (also referred to as a "linear cutter") suitable for use in a variety of cutting and stapling procedures, such as a gastrointestinal anastomosis procedure. Linear surgical stapler (10) includes a cartridge half (12) (also referred to as a "reload half") and an anvil half (14) configured to releasably couple together to clamp tissue therebetween. Cartridge half (12) includes an elongate cartridge channel (16) having a proximal frame portion (18) that slidably retains a portion of a firing assembly (34), a distal jaw portion (20) that supports a staple cartridge (80) (or "reload"), and a pair of upright side flanges (22) arranged medially therebetween.

Cartridge half (12) further includes a clamp lever (24) (also known as a "closure handle") pivotably coupled to an underside of cartridge channel (16) in approximate alignment with side flanges (22). Clamp lever (24) includes an elongate lever arm (26) having a free proximal end and a distal end that is pivotably coupled to cartridge channel (16) with a pivot pin (28). A pair of opposed jaws (30) (also referred to as "hook latches") extend distally from the distal end of lever arm (26) alongside flanges (22) of cartridge channel (16). Each jaw (30) includes a respective elongate slot (32) having a closed proximal end and an open distal end, and which defines upper and lower camming surfaces configured to engage a respective latch projection (56) of anvil half (14). As described below, clamp lever (24) is operable to pivot relative to cartridge channel (16) between open and closed positions to releasably clamp anvil half (14) against cartridge half (12) and thereby capture tissue layers therebetween.

As shown best in FIG. 2, firing assembly (34) of cartridge half (12) includes a slider block (36) slidably retained within proximal frame portion (18) of cartridge channel (16), an actuator (38) (or "firing knob") movably coupled with slider block (36), and an elongate actuating beam (not shown) extending distally from slider block (36) and configured to couple with a sled (100) (see FIG. 3) housed within staple cartridge (80). Actuator (38) of the present example is configured to pivot about the proximal end of cartridge half (12) to provide for "dual-sided firing" of stapler (10). Specifically, actuator (38) may be positioned along either lateral side of cartridge half (12) to perform a distal firing stroke, such that stapler (10) may be conveniently fired in a variety of orientations during a surgical procedure.

Figure 5A:
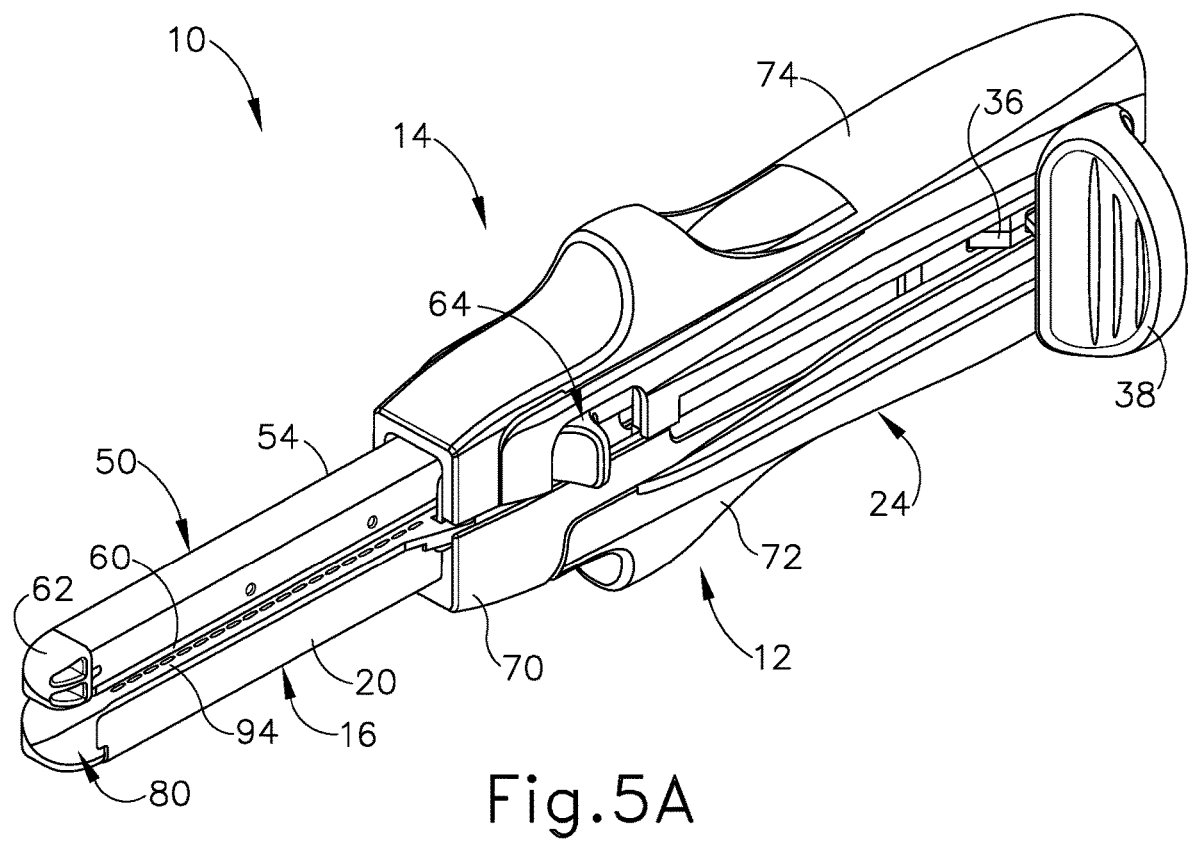
FIG. 5A depicts a distal perspective view of the linear surgical stapler of FIG. 1, showing an actuator of the stapler in a proximal, pre-fired position.
Figure 5B:
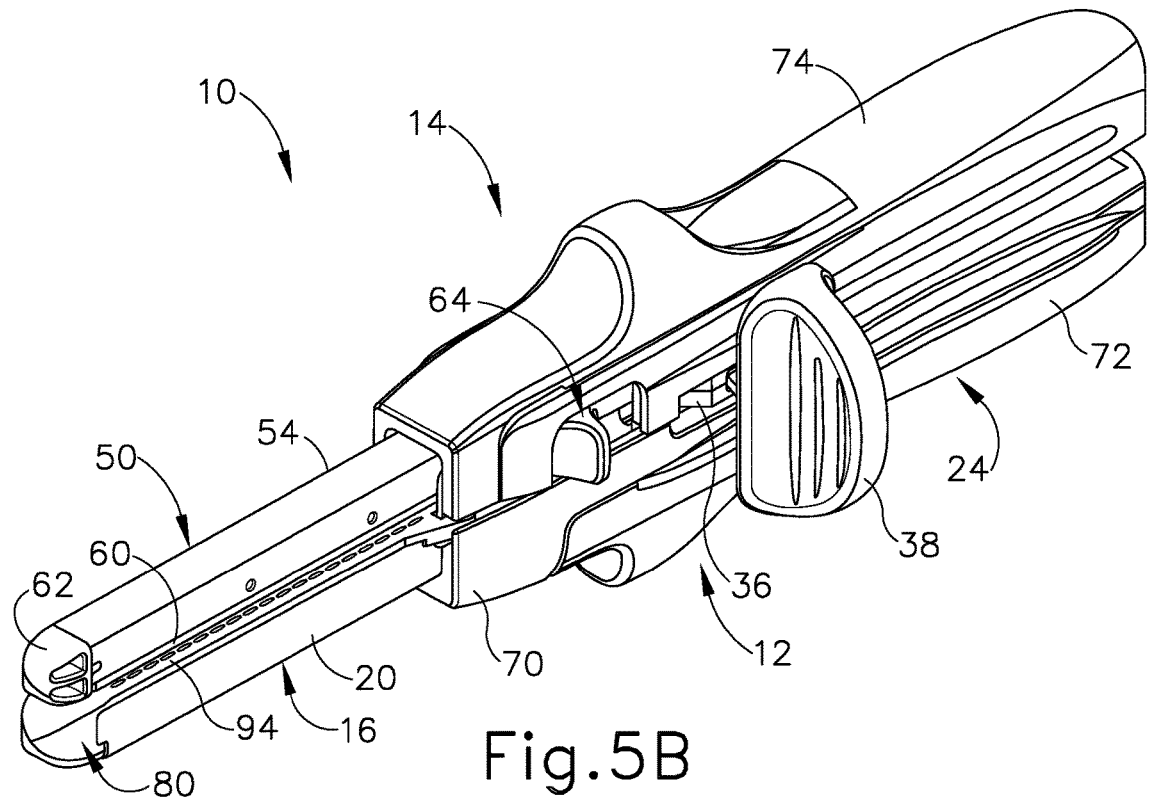
FIG. 5B depicts a distal perspective view of the linear surgical stapler of FIG. 1, showing the actuator in a distal, fired position.

Slider block (36) is configured to be translatably driven within proximal frame portion (18) by actuator (38) between a proximal home position shown in FIGS. 2 and 5A, and a distal fired position shown in FIG. 5B. In the proximal home position, slider block (36) abuts a post (40) fixed at a proximal end of cartridge channel (16). A free end of post (40) supports a laterally extending pivot pin (42). As described below, actuator (38) may be driven distally when stapler halves (12, 14) are fully coupled together and clamp lever (24) is closed. Distal advancement of actuator (38) along either lateral side of stapler (10) drives slider block (36) and the elongate actuating beam distally, which in turn drives sled (100) distally through staple cartridge (80). As described below, distal translation of sled (100) through staple cartridge (80) provides for simultaneous stapling and cutting of tissue clamped between stapler halves (12, 14).

As shown best in FIGS. 1 and 2, anvil half (14) of linear surgical stapler (10) includes an elongate anvil channel (50) having a proximal frame portion (52) and a distal jaw portion (54). Anvil channel (50) further includes a latch feature in the form of a pair of projections (56) that extend transversely from a medial portion of anvil channel (50) in a direction toward cartridge half (12). Each latch projection (56) may include a circular rotating cap configured to be captured within the slot (32) of a respective clamp lever jaw (30) when anvil half (14) is coupled with cartridge half (12) and clamp lever (24) is pivoted from the open position to the closed position, as described below. A pair of hooks (58) extend proximally from a proximal end of frame portion (52) and are configured to releasably capture opposed lateral ends of proximal pivot pin (42) of cartridge half (12). Distal jaw portion (54) supports an anvil surface in the form of an anvil plate (60) having a plurality of staple-forming pockets (not shown), and additionally supports a distal tip member (62). In other versions of stapler (10), the anvil surface may be formed integrally with or otherwise be rigidly connected to distal jaw portion (54) of anvil channel (50). In the present version, each of anvil channel (50) and cartridge channel (16) is a monolithic structure formed of a metal, such as stainless steel, that provides rigidity to the respective stapler half (12, 14).

Anvil half (14) of the present example further includes a staple height adjustment mechanism (64) mounted to a medial portion of anvil channel (50). Staple height adjustment mechanism (64) is operatively coupled with anvil plate (60), for example via one or more camming features (not shown), and includes a pair of user-engageable projections (66). Longitudinal adjustment of projections (66) between a plurality of predetermined positions causes anvil plate (60)

to move transversely relative to distal jaw portion (54) of anvil channel (50). This enables adjustment of a transverse gap distance between anvil plate (60) and a deck (94) of staple cartridge (80) that defines the height of staples being formed. A larger gap distance, and thus a greater staple height, may be set when stapling tissues of greater thicknesses. Conversely, a smaller gap distance, and thus a smaller staple height, may be set when stapling tissues of lesser thicknesses. It will be appreciated that staple height adjustment mechanism (64) may be omitted in some versions, in which case the anvil surface may be fixed relative to anvil channel (50). For instance, the anvil surface may be formed integrally with or otherwise fixedly secured to distal jaw portion (54).

As shown best in FIGS. 1 and 2, linear surgical stapler (10) further includes a plurality of shrouds (70, 72, 74) that cover select portions of stapler (10) and promote effective grip and manipulation of stapler (10) by an operator during use. In the present example, cartridge half (12) includes a first shroud (70) that covers an outwardly facing side of proximal frame portion (18) of cartridge channel (16). Cartridge half (12) further includes a second shroud (72) that covers an outwardly facing side of clamp lever (24) and is configured to pivot with clamp lever (24) relative to cartridge channel (16) and first shroud (70). Anvil half (14) includes a third shroud (74) that covers an outwardly facing side of proximal frame portion (52) of anvil channel (50), including proximal hooks (58). Each shroud (70, 72, 74) may be coupled with its respective components of stapler (10) by any suitable means apparent to those of ordinary skill in the art. Additionally, each shroud (70, 72, 74) may be formed of one or more materials and be provided with texturing suitable to promote effective gripping of the shroud (70, 72, 74) by an operator to enable safe and efficient use of stapler (10) during a surgical procedure.

As shown in FIGS. 2 and 3, staple cartridge (80) of the present example is an assembly that comprises a cartridge body (82), a pan (84) that covers an open lower side of cartridge body (82), and a plurality of staple drivers (86) housed within cartridge body (82) and each being configured to drive a respective staple (88). Cartridge body (82) includes a proximal end having coupling features (90) configured to releasably engage corresponding coupling features (not shown) of distal jaw portion (20) of cartridge channel (16), and a distal end defining a tapered nose (92). An upper side of cartridge body (82) defines a generally planar deck (94) through which a longitudinal slot (96) and a plurality of staple cavities (98) open. Each staple cavity (98) houses a respective staple driver (86) and a staple (88). As shown in FIG. 3, an interior of cartridge body (82) slidably houses a sled (100) that comprises a sled body (102) and knife member (104). Lateral sides of sled body (102) support a plurality of cam ramps (106) that taper distally. A proximal end of sled body (102) includes a downwardly extending tab (108) configured to lockingly engage a distal end of the elongate actuating beam (or "knife pusher") (not shown) of firing assembly (34) when staple cartridge (80) is mounted to cartridge half (12) of stapler (10). Knife member (104) extends upwardly from an upper side of sled body (102) and presents a distally facing cutting edge (110) configured to cut tissue.

Sled (100) is configured to translate distally through cartridge body (82) in response to distal actuation of firing assembly (34), such that knife member (104) translates distally through longitudinal slot (96) to cut tissue clamped between stapler halves (12, 14). Simultaneously, cam ramps (106) translate distally through respective interior slots (not shown) of cartridge body (82) to actuate staple drivers (86) and staples (88) upwardly through staple cavities (98) so that free ends of staples (88) pierce through the clamped tissue and deform against staple-forming pockets of anvil plate (60). In this manner, distal actuation of firing assembly (34) provides for simultaneous severing and stapling of tissue clamped between the distal end effector portions of stapler halves (12, 14).

Linear surgical stapler (10) and staple cartridge (80) may be further configured and operable in accordance with one or more teachings of U.S. Pat. No. 7,905,381, entitled "Surgical Stapling Instrument with Cutting Member Arrangement," issued Mar. 15, 2011; U.S. Pat. No. 7,954,686, entitled "Surgical Stapler with Apparatus for Adjusting Staple Height," issued Jun. 7, 2011; U.S. Pat. No. 8,348,129, entitled "Surgical Stapler Having A Closure Mechanism," issued Jan. 8, 2013; and/or U.S. Pat. No. 8,789,740, entitled "Linear Cutting and Stapling Device with Selectively Disengageable Cutting Member," issued Jul. 29, 2014. The disclosure of each of these references is incorporated by reference herein.

B. Exemplary Use of Linear Surgical Stapler

Figure 4A:
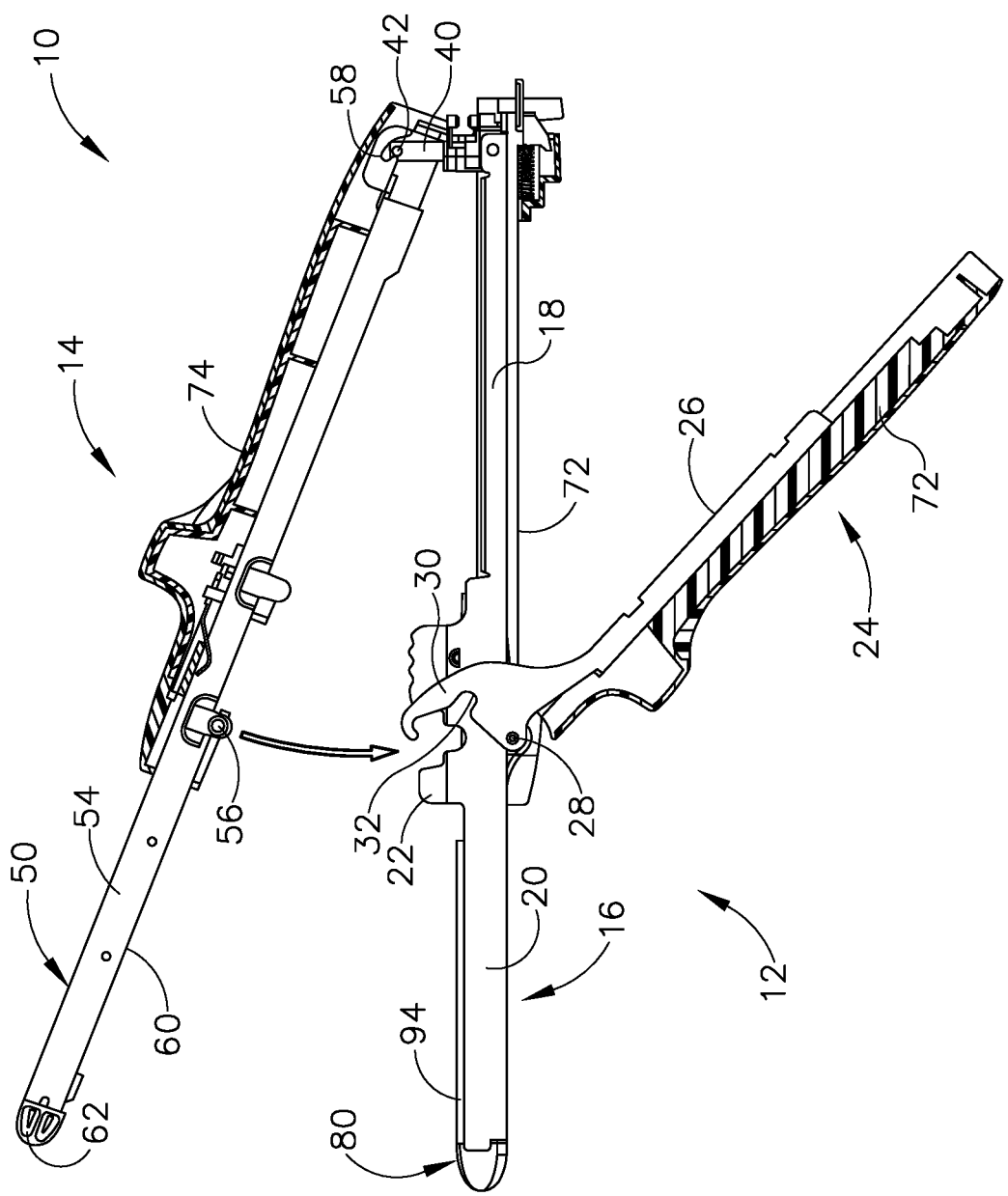
FIG. 4A depicts a cross-sectional side view of the linear surgical stapler of FIG. 1, showing the stapler halves coupled together at their proximal ends with the clamp lever in an open position.
Figure 4B:
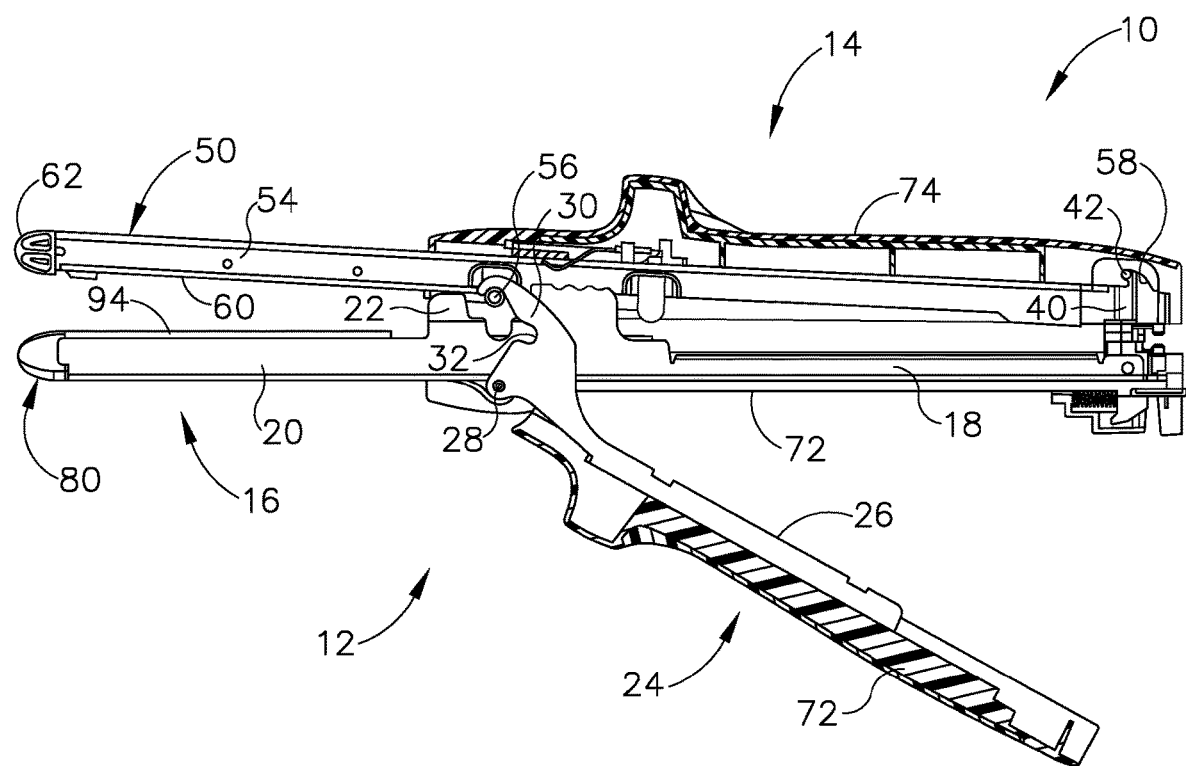
FIG. 4B depicts a cross-sectional side view of the linear surgical stapler of FIG. 1, showing the stapler halves coupled together with the clamp lever in a partially closed position.
Figure 4C:
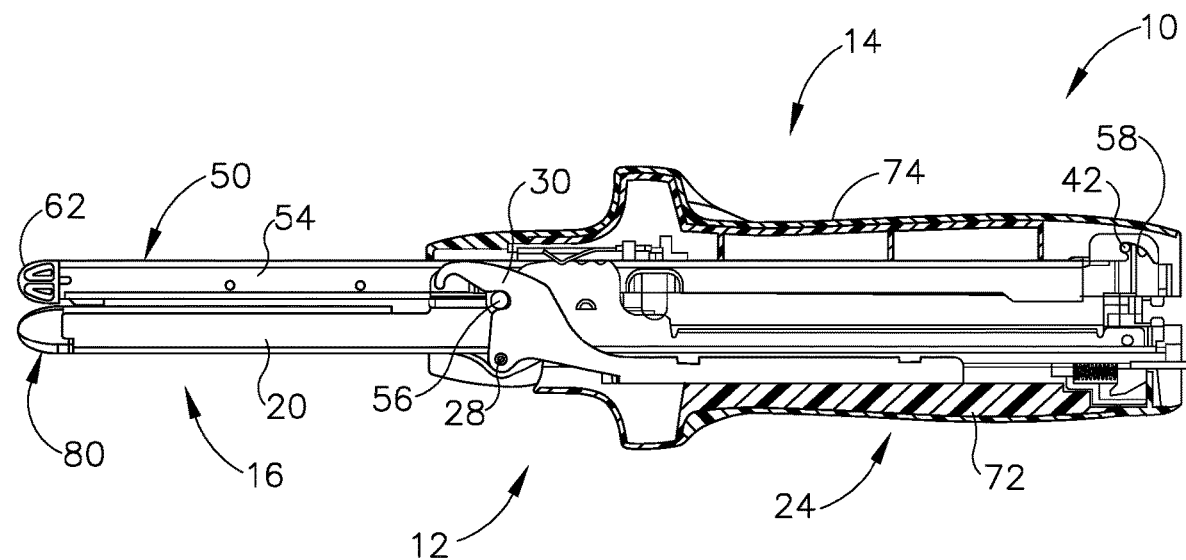
FIG. 4C depicts a cross-sectional side view of the linear surgical stapler of FIG. 1, showing the stapler halves coupled together with the clamp lever in a fully closed position.

FIGS. 4A-4C show exemplary coupling of stapler halves (12, 14) during a surgical procedure. As shown in FIG. 4A, the proximal end of anvil half (14) is aligned with the proximal end of cartridge half (12) such that proximal pivot pin (42) of cartridge half (12) is received by proximal hooks (58) of anvil half (14). With clamp lever (24) in the open position, anvil half (14) is then pivoted toward cartridge half (12), about proximal pivot pin (42), to direct latch projections of anvil half (14) into slots (32) of clamp lever jaws (30). Once latch projections (56) are received by clamp lever jaws (30), clamp lever (24) is pivoted toward the partially closed position shown in FIG. 4B. In this partially closed position of clamp lever (24), anvil half (14) is partially clamped with cartridge half (12) such that stapler (10) may now be held with a single hand without halves (12, 14) undesirably separating from one another. Additionally, in this state, the distal portions of stapler halves (12, 14) remain spaced apart from one another to permit positioning of tissue between the distal portions. It will be appreciated that tissue may be positioned between the distal portions of stapler halves (12, 14) before or upon achieving this partially clamped state.

As shown in FIG. 4C, clamp lever (24) is then pivoted further toward its fully closed position such that the camming surfaces of clamp lever jaws (30) draw latch projections of anvil half (14) proximally against the closed proximal ends of slots (32) of clamp lever jaws (30), thereby fully clamping stapler halves (12, 14) together with tissue positioned securely therebetween. Once halves (12, 14) of stapler (10) are in a fully clamped state, actuator (38) may be manipulated to fire staple cartridge (80). In particular, as shown in FIGS. 5A and 5B, actuator (38) is pivoted about the proximal end of stapler (10) to overlie one of the lateral sides of stapler (10). Actuator (38) is then driven distally to actuate firing assembly (34) in the manner described above and thereby simultaneously sever and staple the clamped tissue. Upon completing a distal firing stroke, actuator (38) may be returned to its proximal home position shown in FIG. 2, and clamp lever (24) may then be opened to separate stapler halves (12, 14) from one another and release the stapled and severed tissue.

II. Exemplary Linear Surgical Staplers Having Closure Lockout Features

As described above in connection with linear surgical stapler (10), anvil half (14) is assembled with cartridge half

(12) such that latch projections (56) of anvil half (14) are received within vertical slots defined by side flanges (22) of cartridge channel (16). Clamp lever (24) is then pivoted from an open position to a closed position to capture latch projections (56) and thereby clamp anvil half (14) against cartridge half (12). As shown in FIG. 4A, clamp lever (24) must be maintained in the open position manually by the user to prevent premature closure and permit latch projections (56) to be properly received by the vertical slots of cartridge channel (16) and jaws (30) of clamp lever (24).

In some instances, it may be desirable to provide a linear surgical stapler with features that ensure the clamp lever is automatically maintained in the open position and does not rotate closed until the stapler halves are sufficiently approximated such that the latch projections of the anvil half are positioned to be captured by features of the cartridge half. The exemplary linear surgical staplers (200, 300, 400) described below each have a configuration that provides such benefits.

Figure 6:
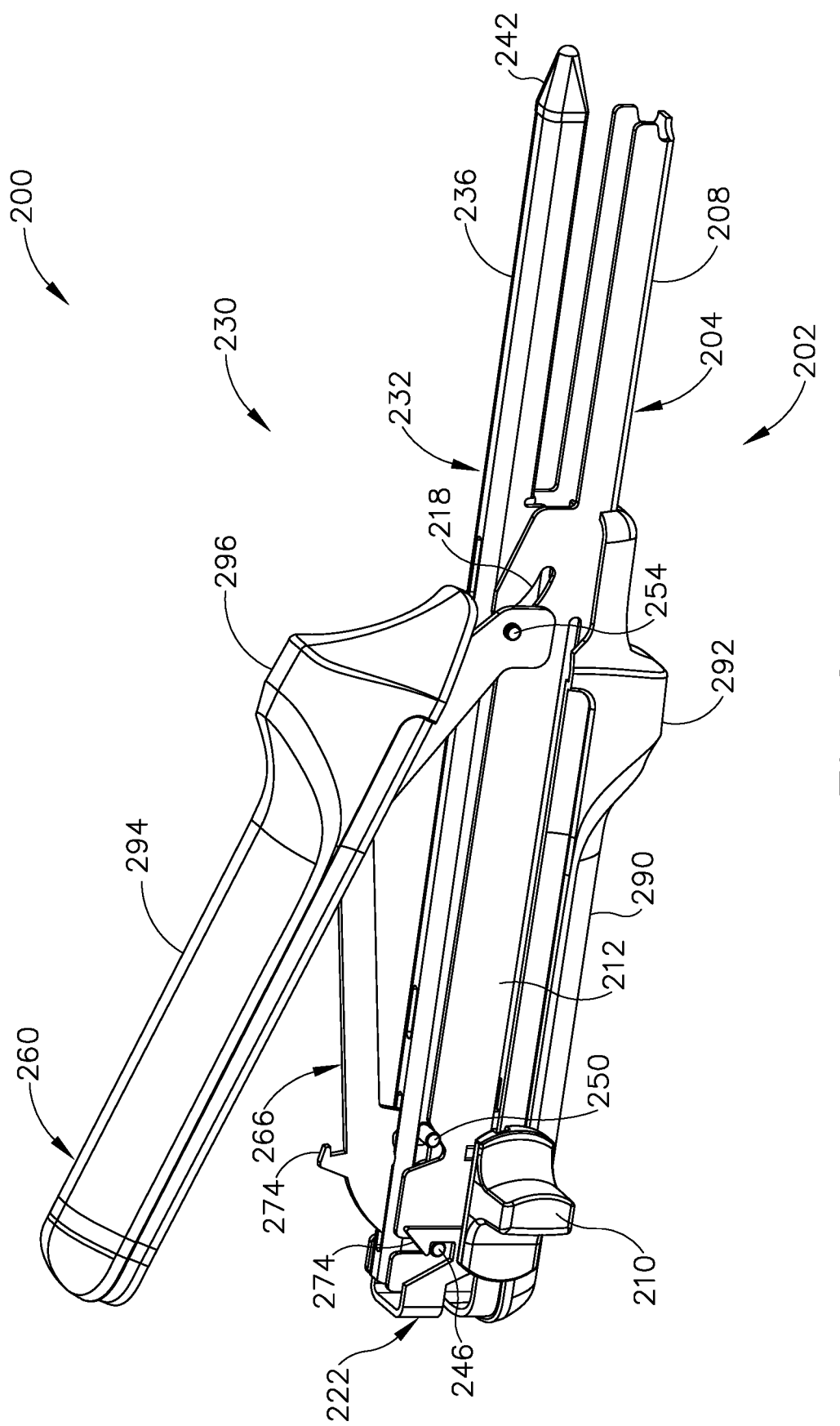
FIG. 6 depicts a perspective view of another exemplary linear surgical stapler.
Figure 7:
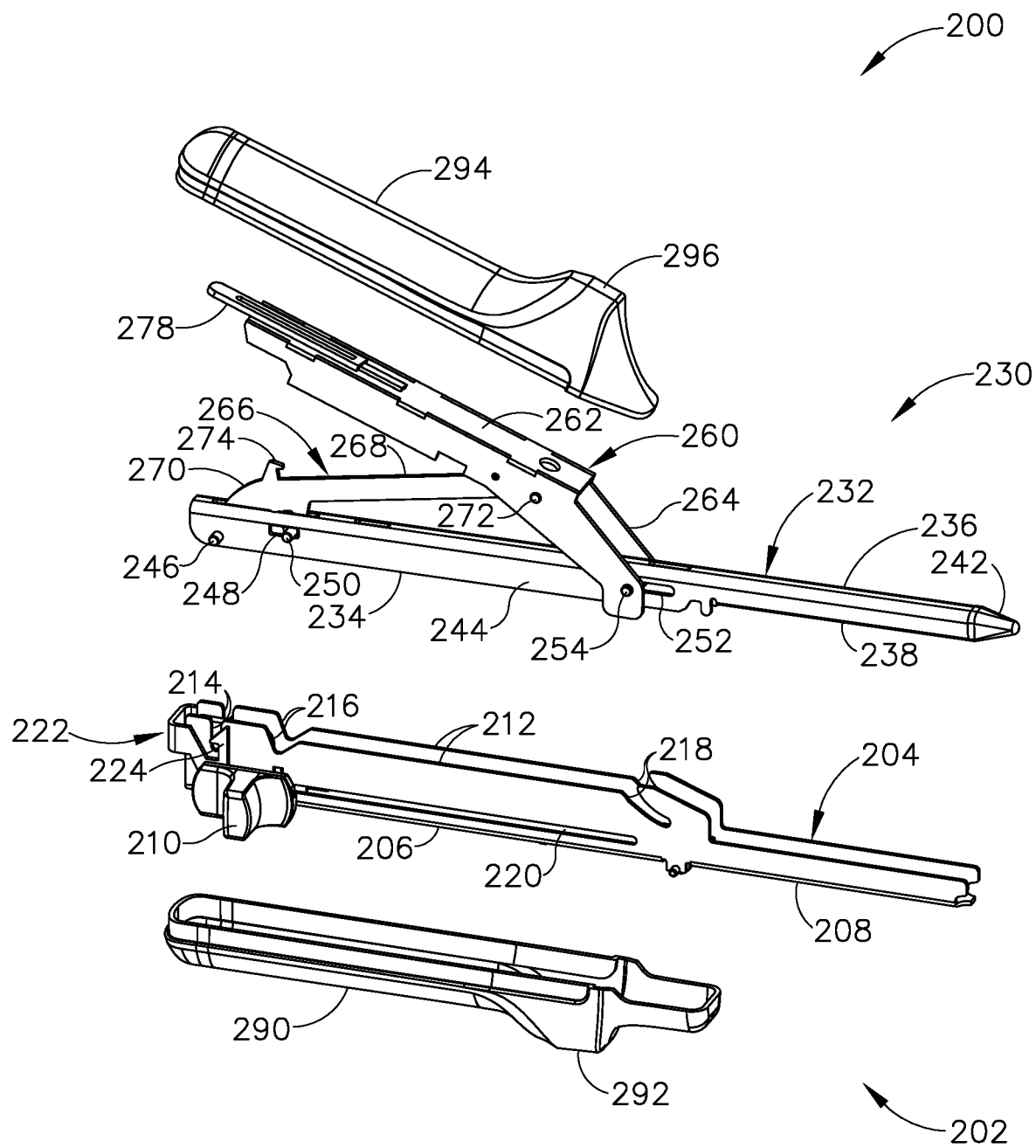
FIG. 7 depicts a partially-exploded perspective view of the linear surgical stapler of FIG. 6.

A. Exemplary Linear Surgical Stapler Having Clamp Lever and Closure Lockout Pin on Anvil Half FIGS. 6 and 7 show an exemplary linear surgical stapler (200) (or "linear cutter") that is generally similar linear surgical stapler (10) described above except as otherwise described below. Linear surgical stapler (200) includes a cartridge half (202) and an anvil half (230) configured to releasably couple together to clamp tissue therebetween and simultaneously cut and staple the clamped tissue.

Cartridge half (202) of stapler (200) includes an elongate cartridge channel (204) having a proximal frame portion (206) and a distal jaw portion (208). Proximal frame portion (206) slidably retains a firing assembly having a firing knob (210) and includes a laterally opposed pair of upright side flanges (212). Each side flange (212) includes a vertical slot (214) arranged at a proximal end of side flange (212), a v-shaped notch (216) arranged distally of vertical slot (214), and a curved cam slot (218) arranged at a distal end of side flange (212). In the present version, one of the side flanges (212) further includes a longitudinally extending firing slot (220) through which a portion of firing knob (210) extends inwardly to couple with a translating member (not shown) of the firing assembly. Firing slot (220) enables firing knob (210) to translate longitudinally relative to cartridge channel (204) between from a proximal position to a distal position to actuate the firing assembly and thereby fire a staple cartridge (not shown) mounted within distal jaw portion (208). The firing assembly and the staple cartridge may be configured in accordance with any one or more of the teachings incorporated by reference herein. In some versions, the staple cartridge may be similar to staple cartridge (80) described above.

Cartridge half (202) further includes a proximal latch member (222) coupled to the exterior of a proximal end of cartridge channel (204). Proximal latch member (222) includes a pair of vertically projecting latch hooks (224) and is configured to translate relative to cartridge channel (204) between a proximal latching position, shown in FIG. 7, and a distal release potion. In the proximal latching position, each latch hook (224) is configured to capture a respective lateral end of a proximal pivot pin (246) of anvil half (230), thereby coupling the proximal ends of cartridge half (202) and anvil half (230) together. In the release position, latch hooks (224) release proximal pivot pin (246) so that the proximal ends of stapler halves (202, 230) may be separated. In the present version, proximal latch member (222) is resiliently biased toward the proximal latching position. Additionally, each latch hook (224) includes a proximally sloped upper surface configured to cam proximal latch member (222) distally upon initial engagement with proximal pivot pin (246) during the coupling of the proximal ends of stapler halves (202, 230).

Anvil half (230) of linear surgical stapler (200) includes an elongate anvil channel (232) having a proximal frame portion (234) and a distal jaw portion (236). As shown in FIG. 8, an underside of distal jaw portion (236) supports an anvil surface (238) having a plurality of staple-forming pockets (240) (or "anvil pockets") configured to form staples ejected by a staple cartridge (not shown) mounted within distal jaw portion (208) of cartridge channel (204). Anvil surface (238) of the present version is formed integrally with distal jaw portion (236), though in other versions anvil surface (238) may be formed separately from anvil channel (232) and subsequently coupled to distal jaw portion (236) via permanent or releasable joining features. A tapered distal tip member (242) extends distally from a distal jaw portion (236).

Proximal frame portion (234) of anvil channel (232) includes a laterally opposed pair of side flanges (244) configured to be received between cartridge channel side flanges (212) when cartridge half (202) and anvil half (230) are coupled together in the manner described below. Anvil channel side flanges (244) include a pair of openings arranged at a proximal end thereof and which receive a first coupling element in the form of a first pin (246) (also referred to herein as a "pivot pin") laterally therethrough. Anvil channel side flanges (244) further include a first pair of elongate slots (248) arranged distally of first pin (246) and which receive a second coupling element in the form of a second pin (250) (also referred to herein as a "lockout pin") that extends laterally therethrough and is slidable longitudinally therein. A second pair of elongate slots (252) is arranged at a distal end of anvil channel side flanges (244) and receives a third coupling element in the form of a third pin (254) (also referred to as a "clamp pin" or "latch pin") that extends laterally therethrough and is slidable longitudinally therein. As described in greater detail below, lockout pin (250) and clamp pin (254) are configured to translate longitudinally within their respective elongate slots (248, 252) to facilitate clamping of stapler halves (202, 230) together.

As shown best in FIGS. 7 and 9, anvil half (230) further includes an elongate clamp lever (260) having a proximal handle portion (262) and a distal angled portion (264) pivotably coupled to a distal end of proximal frame portion (234) with clamp pin (254). As described below, clamp lever (260) is configured to pivot relative to anvil channel (232) from an open position to a closed position to clamp stapler halves (202, 230) together. Anvil half (230) further includes an elongate closure link (266) having a linear distal link portion (268) and an angled proximal link portion (270). A distal end of distal link portion (268) is pivotably coupled to a distal end of clamp lever handle portion (262) by a laterally extending pin (272). A proximal end of proximal link portion (270) is pivotably coupled to a proximal end of anvil channel (232) with pivot pin (246) described above. Accordingly, closure link (266) is configured to pivot relative to anvil channel (232) and clamp lever (260) in response to pivoting of clamp lever (260) between its open and closed positions.

The junction between proximal link portion (270) and distal link portion (268) of closure link (266) includes an upwardly extending latch hook (274) and downwardly extending tab (276). When clamp lever (260) is closed, as shown in FIGS. 10A-10D, latch hook (274) is received through an opening formed in a proximal end of clamp lever handle portion (262) and is captured by a translating latch plate (278), shown in FIG. 7, thereby locking clamp lever (260) in the closed position. Latch plate (278) is slidably coupled to a proximal end of clamp lever handle portion (262) and is configured to translate longitudinally between a proximal latching position and a distal release position. Latch plate (278) is resiliently biased toward the proximal latching position and is cammed distally by a sloped upper surface of latch hook (274) when clamp lever (260) is closed, such that latch hook (274) is captured within an elongate slot of latch plate (278). A proximal end of latch plate (278) extends proximally beyond a proximal end of clamp lever (260), as shown in FIG. 7, and is configured to be actuated distally by a user to release latch hook (274) from latch plate (278) and permit opening of clamp lever (260).

As shown in FIG. 9, lockout pin (250) extends laterally through a proximal translating clevis (280) and clamp pin (254) extends laterally through a distal translating clevis (282). Lockout pin (250) and proximal clevis (280) are resiliently biased distally, and clamp pin (254) and distal clevis (282) are resiliently biased proximally. In the present example, lockout pin (250) and clamp pin (254) are resiliently biased in their respective directions by a shared resilient member in the form of an extension spring (284) that couples at its proximal end to proximal clevis (280) and at its distal end to distal clevis (282). In other versions, each pin (250, 254) and its clevis (280, 282) may be resiliently biased in the respective direction by a respective resilient member.

Lockout pin (250) of anvil half (230) is configured to function as a closure lockout feature that engages closure link (266) to prevent closure of clamp lever (260) unless the proximal ends of stapler halves (202, 230) are coupled together and distal jaw portions (208, 236) are approximated toward one another to a predetermined degree. As shown in FIG. 9, lockout pin (250) and proximal clevis (280) are positioned in a distal lockout position in which lockout pin (250) abuts downward tab (276) of closure link (266). This interaction prevents the distal end of closure link (266) from pivoting toward cartridge channel (204), which in turn prevents clamp lever (260) from fully closing. As described below in connection with FIGS. 10A-10D, lockout pin (250) is configured to be cammed proximally to a release position by v-shaped notches (216) of cartridge channel (204) when distal jaw portions (208, 236) of stapler halves (202, 230) are sufficiently approximated. When in the proximal release position, lockout pin (250) disengages downward tab (276) of closure link (266) and thus permits pivoting of closure link (266) and closure of clamp lever (260). As also described below in connection with FIGS. 10A-10D, closure of clamp lever (260) drives clamp pin (254) distally within longitudinal slots (252) of anvil channel (232) and curved cam slots (218) of cartridge channel (204) to thereby clamp stapler halves (202, 230) together. Upon subsequent opening of clamp lever (260) and separation of stapler halves (202, 230), extension spring (284) contracts such that lockout pin (250) resumes its distal lockout position and clamp pin (254) resumes its proximal position, shown in FIG. 9.

As shown in FIGS. 6 and 7, each stapler half (202, 230) includes a respective shroud configured to promote effective gripping and manipulation of linear surgical stapler (200) by a user. In the present example, cartridge half (202) includes a first shroud (290) that is coupled to and extends longitudinally along outwardly facing surfaces of proximal frame portion (206) of cartridge channel (204). Anvil half (230) includes a second shroud (294) that is coupled to and extends longitudinally along outwardly facing surfaces of proximal handle portion of clamp lever (260). Each shroud (290, 294) of the present example includes a respective distal shoulder (292, 296) configured to further enhance gripping and manipulation of stapler halves (202, 230).

Figure 10A:
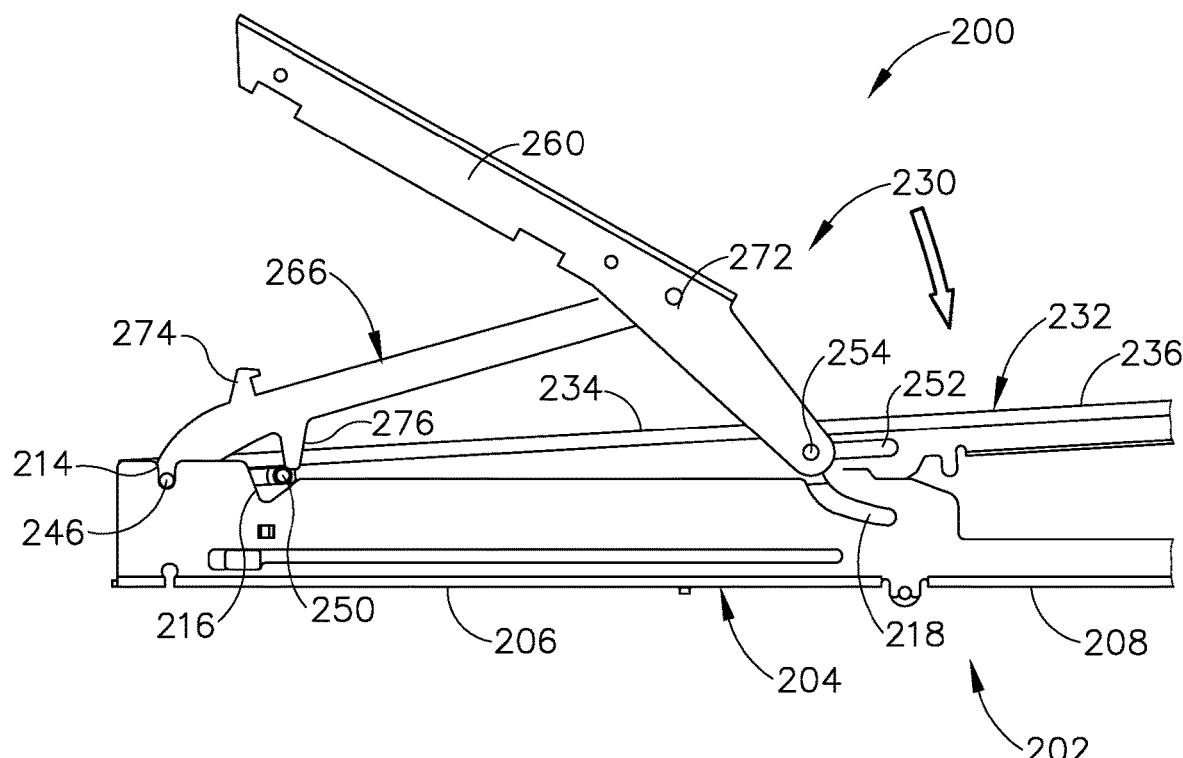
FIG. 10A depicts a side elevational view of the linear surgical stapler of FIG. 6, showing distal portions of the stapler halves being approximated toward one another while a proximal lockout pin of the anvil half is in a lockout position.

FIGS. 10A-10D show an exemplary closure sequence for stapler halves (202, 230) of linear surgical stapler (200). As shown in FIG. 10A, stapler halves (202, 230) are aligned with one another such that proximal pivot pin (246) of anvil half (230) is received within proximal vertical slots (214) of cartridge channel (204). Though not shown in FIGS. 10A-10D, the opposed lateral ends of pivot pin (246) are captured by latch hooks (224) of proximal latch member (222) of cartridge half (202), as seen in FIG. 6, thereby latching the proximal ends of stapler halves (202, 230) together. Additionally, though not shown, a staple cartridge is loaded into distal jaw portion (208) of cartridge channel (204) before stapler halves (202, 230) are brought together.

Figure 10B:
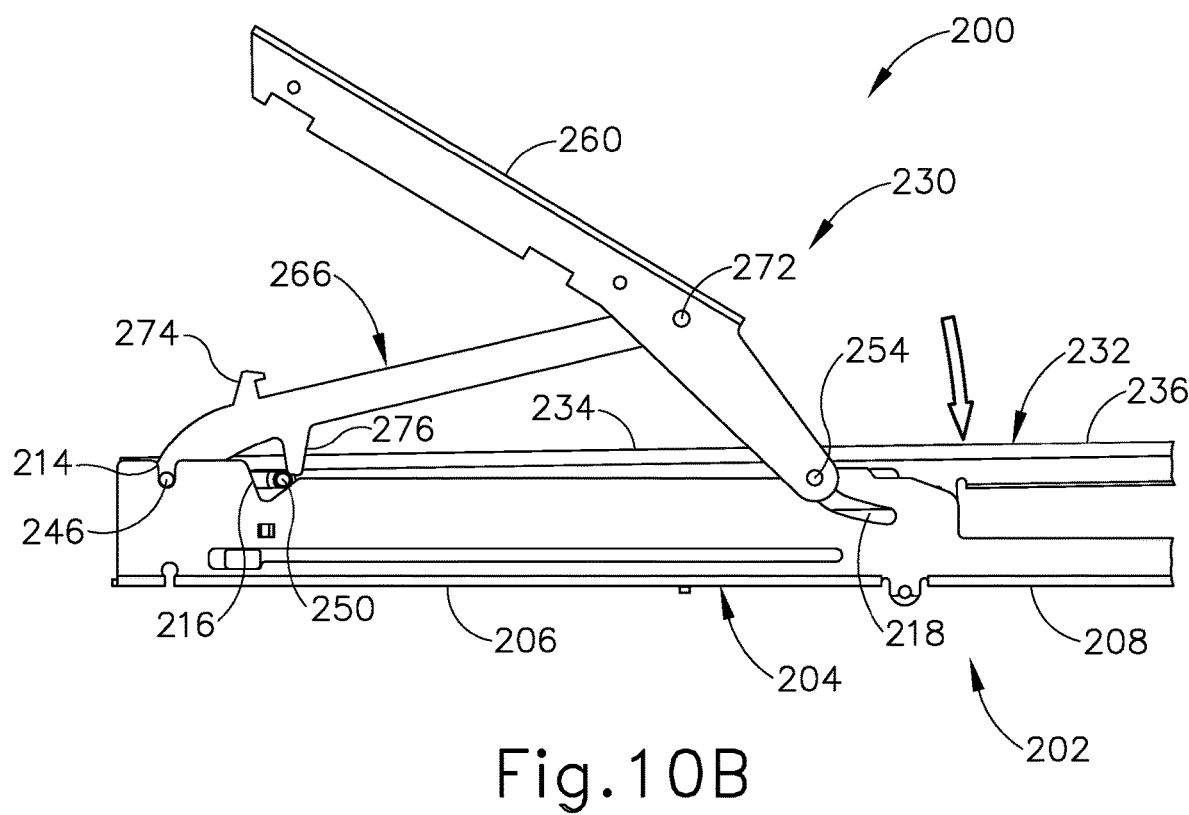
FIG. 10B depicts a side elevational view of the linear surgical stapler of FIG. 6, showing the distal portions of the stapler halves being further approximated so that a proximal cam ramp of the cartridge half actuates the proximal lockout pin of the anvil half proximally to a release position.

At the stage shown in FIG. 10A, lockout pin (250) is in the distal lockout position so that closure link (266) is prevented from pivoting and clamp lever (260) is thus prevented from closing. As shown in FIGS. 10A and 10B, anvil half (230) is then pivoted toward cartridge half (202) about proximal pivot pin (246) such that distal jaw portions (208, 236) of stapler halves (202, 230) are approximated toward one another, which results in distal clamp pin (254) of anvil half (230) being directed into open proximal ends of curved cam slots (218) of cartridge channel (204). The receipt of clamp pin (254) within the open proximal ends of curved cam slots (218) corresponds to a predetermined degree of approximation of distal jaw portions (208, 236). This approximation results in ramped distal surfaces of v-shaped notches (216) in cartridge channel (204) contacting the lateral ends of lockout pin (250) in camming engagement and actuating lockout pin (250) proximally to its release position. In particular, the ramped surfaces of v-shaped notches (216) drive lockout pin (250) proximally such that lockout pin (250) disengages downward tab (276) of closure link (266).

Figure 10C:
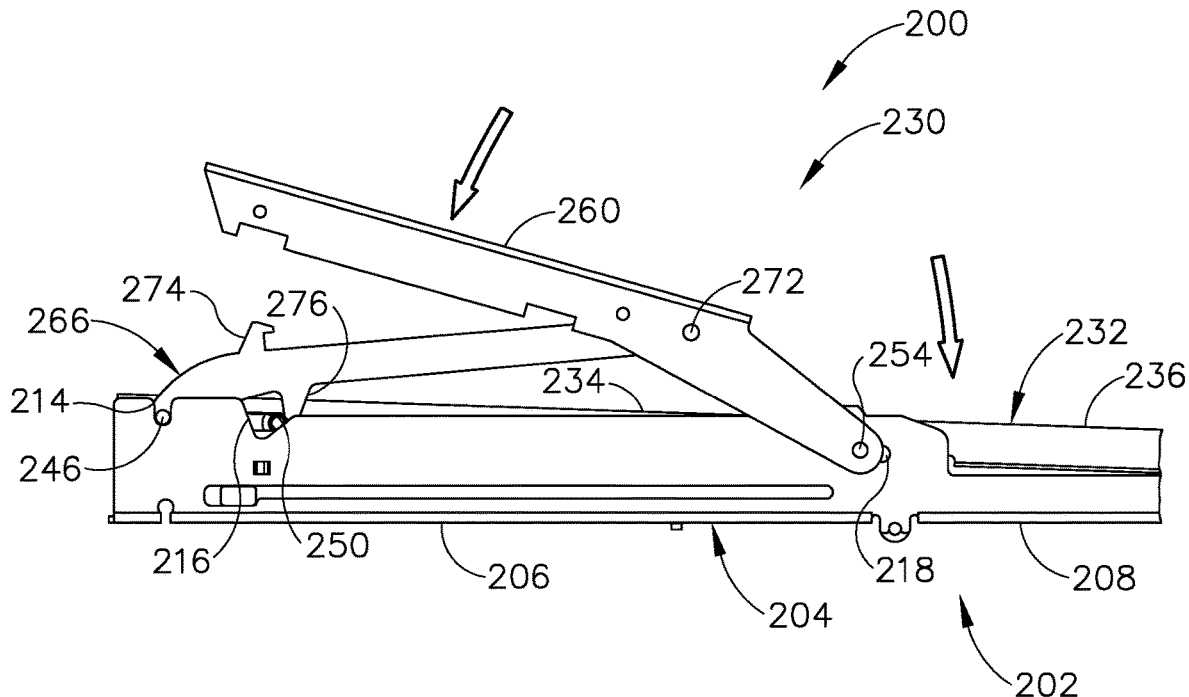
FIG. 10C depicts a side elevational view of the linear surgical stapler of FIG. 6, showing a distal latch pin of the anvil half traveling distally within a cam slot of the cartridge half as a clamp lever of the anvil half is closed.
Figure 10D:
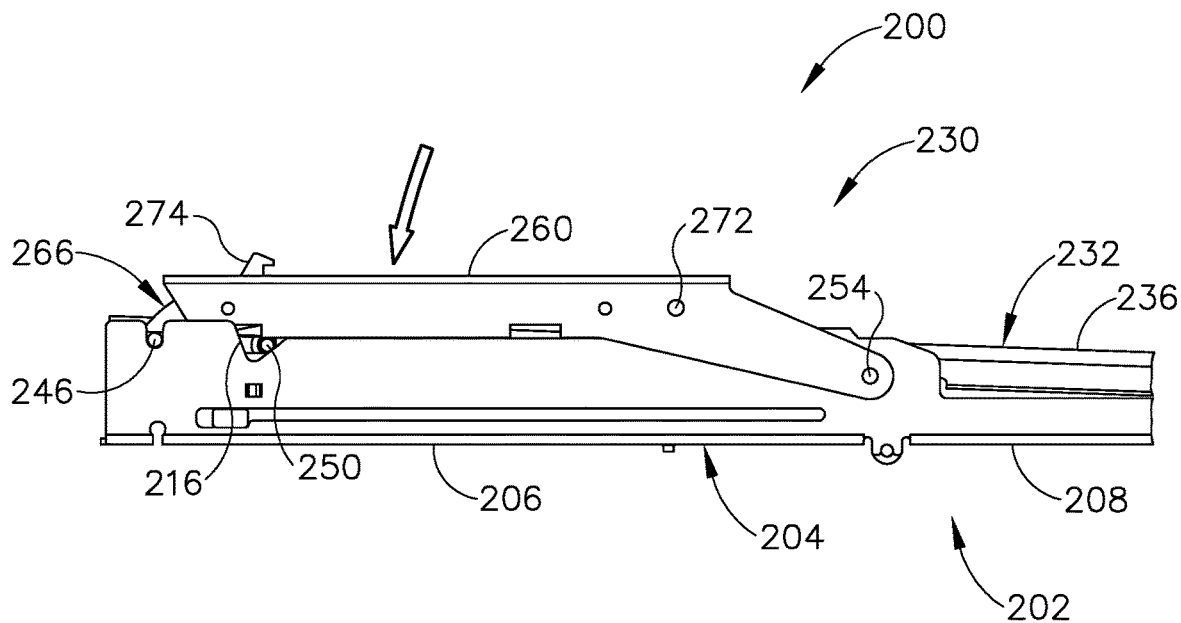
FIG. 10D depicts a side elevational view of the linear surgical stapler of FIG. 6, showing the clamp lever in a fully closed position.

As shown in FIG. 10C, closure link (266) is now free to pivot relative to anvil channel (232) such that clamp lever (260) may pivot about clamp pin (254) toward its closed position. As shown in FIGS. 10C and 10D, closure of clamp lever (260) drives clamp pin (254) distally within cam slots (218) of cartridge channel (204), thereby clamping anvil half (230) against cartridge half (202) and compressing tissue (not shown) positioned between distal jaw portions (208, 236). As described above, distal elongate slots (252) of anvil channel (232) enable clamp pin (254) to translate distally relative to anvil channel (232) in response to simultaneous pivoting of closure link (266) and closure of clamp lever (260). Accordingly, the configuration of stapler (200) described above provides mechanical advantage via clamp lever (260), while avoiding unintended premature closure of clamp lever (260) via a clamp lever lockout system defined by lockout pin (250) and closure link (266).

Figure 11A:
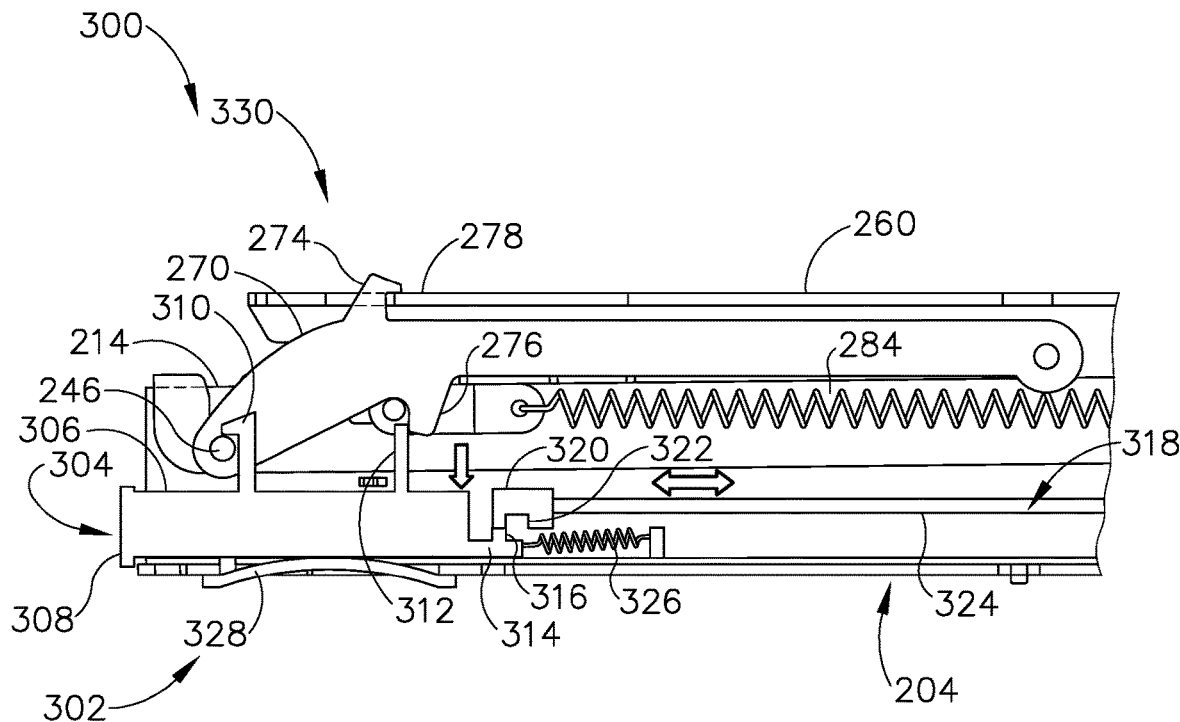
FIG. 11A depicts a schematic side view of a proximal portion of another exemplary linear surgical stapler, showing a button member of the cartridge half in a proximal position when the clamp lever is closed.
Figure 11B:
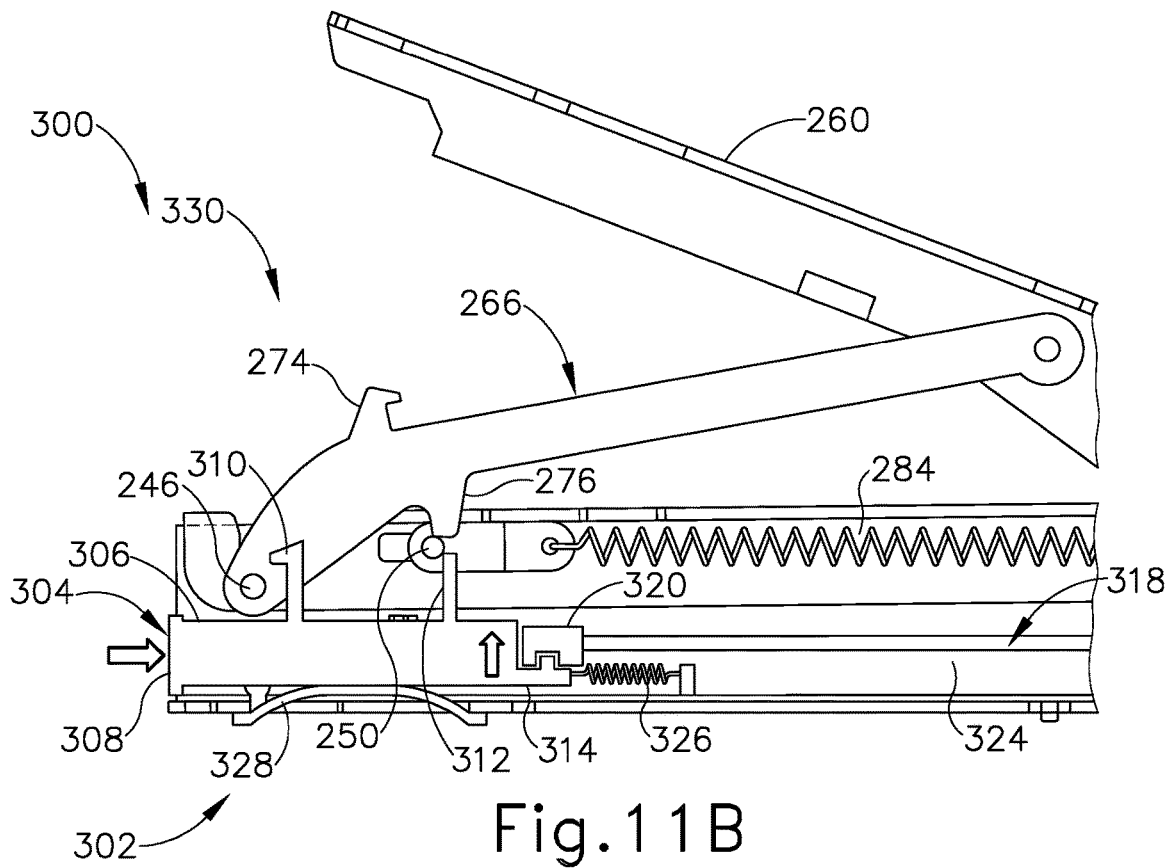
FIG. 11B depicts a schematic side view of a proximal portion of the linear surgical stapler of FIG. 11A, showing the button member actuated to a distal position after the clamp lever is opened.

B. Exemplary Linear Surgical Stapler Having Button Member That Provides Firing Lockout and Proximal Latch Feature In some instances, it may be desirable to provide linear surgical stapler (200) with additional features that prevent distal actuation of the firing assembly until clamp lever (260) is fully closed. FIGS. 11A and 11B show a proximal end of an exemplary alternative linear surgical stapler (300) that includes such features. Stapler (300) includes a cartridge half (302) and an anvil half (330) that are similar to cartridge half (202) and anvil half (230) described above, as indicated by use of like references numerals, except as otherwise described below.

Cartridge half (302) of the present example omits the externally-mounted proximal latch member (222) of stapler (200) described above, and instead includes an internally-mounted button member (304) arranged within a proximal end of proximal frame portion (206) of cartridge channel (204). Button member (304) of the present example includes a block-like body (306) having a proximal end that defines a push-button feature (308), which is exposed through an opening in the proximal end of stapler (300). A latch hook (310) extends upwardly from a medial portion of body (306) and faces proximally; and is configured to engage pivot pin (246) of anvil half (330). A post (312) extends upwardly from a distal portion of body (306) and is configured to engage a proximal face of downward tab (276) of closure link (266). A distal extension (314) extends distally from body (306) and includes an upwardly extending tab (316) configured to engage a pusher block (320) of firing assembly (318). Pusher block (320) includes a notch (322) and is coupled to an elongate actuating beam (324) (or "knife pusher") configured to drive a knife and staple drive features (not shown) through a staple cartridge.

Button member (304) is longitudinally movable within cartridge channel (204) between proximal and distal positions, and transversely movable between raised and lowered positions. Distal extension (314) of button member (304) is coupled to a first resilient member in the form of a compression spring (326) that biases button member (304) proximally. A second resilient member in the form of a leaf spring (328) engages the underside of button member (304) and biases button member (304) upwardly. Accordingly, compression spring (326) and leaf spring (328) cooperate to resiliently bias button member (304) toward a proximal raised position.

In the proximal raised position of button member (304), latch hook (310) is aligned longitudinally with vertical slots (214) of cartridge channel (204). Accordingly, when proximal pivot pin (246) of anvil half (330) is directed downwardly into vertical slots (214), pivot pin (246) cams against a sloped upper surface of latch hook (310) and drives button member (304) distally. As pivot pin (246) surpasses the upper portion of latch hook (310), button member (304) snaps back proximally via compression spring (326) so that latch hook (310) captures pivot pin (246) and prevents the proximal ends of stapler halves (302, 330) from separating. As clamp lever (260) is closed, closure link (266) pivots downwardly such that downward tab (276) of closure link (266) contacts and urges button member (304) downwardly against the upward bias of leaf spring (328), yielding the configuration shown in FIG. 11A. In this proximal lowered position of button member (304), post (312) abuts a proximal side of downward tab (276), thereby locking button member (304) in the proximal position and preventing release of pivot pin (246) from latch hook (310) while clamp member (260) remains closed. Additionally, while button member (304) is in the proximal lowered position, distal tab (316) is disengaged from pusher block (320), such that firing assembly (318) may be actuated distally by firing knob (210) (see FIG. 6) to fire stapler (300).

As shown in FIG. 11B, upon reopening of clamp lever (260) after firing, downward tab (276) of closure link (266) disengages button member (304), thereby allowing button member (304) to rise via the bias of leaf spring (328). This causes distal tab (316) to engage notch (322) in the underside of pusher block (320), thereby locking out firing assembly (318) and preventing it from being actuated distally by firing knob (210) while clamp lever (260) while remains opening. As also shown in FIG. 11B, downward tab (276) of closure link (266) has disengaged post (312) of button member (304) so that button member (304) may be actuated distally by a user via push-button feature (308), which results in latch hook (310) releasing proximal pivot pin (246) of anvil half (230) so that the proximal ends of stapler halves (302, 330) may be separated.

Figure 12:
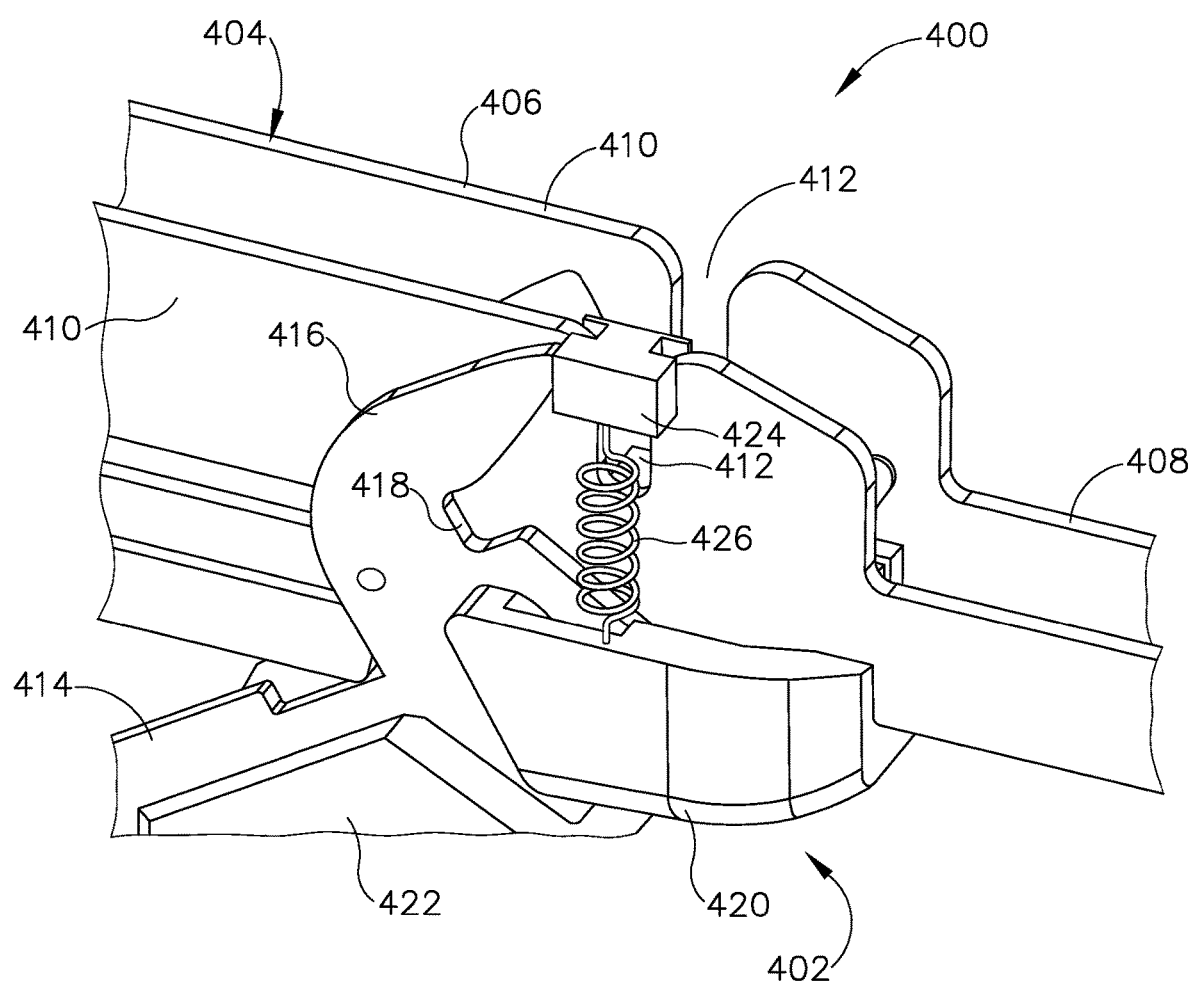
FIG. 12 depicts a perspective view of a clamping portion of another exemplary linear surgical stapler, showing a blocking element in an extended blocking position in which the blocking element prevents closure of the clamp lever.
Figure 13A:
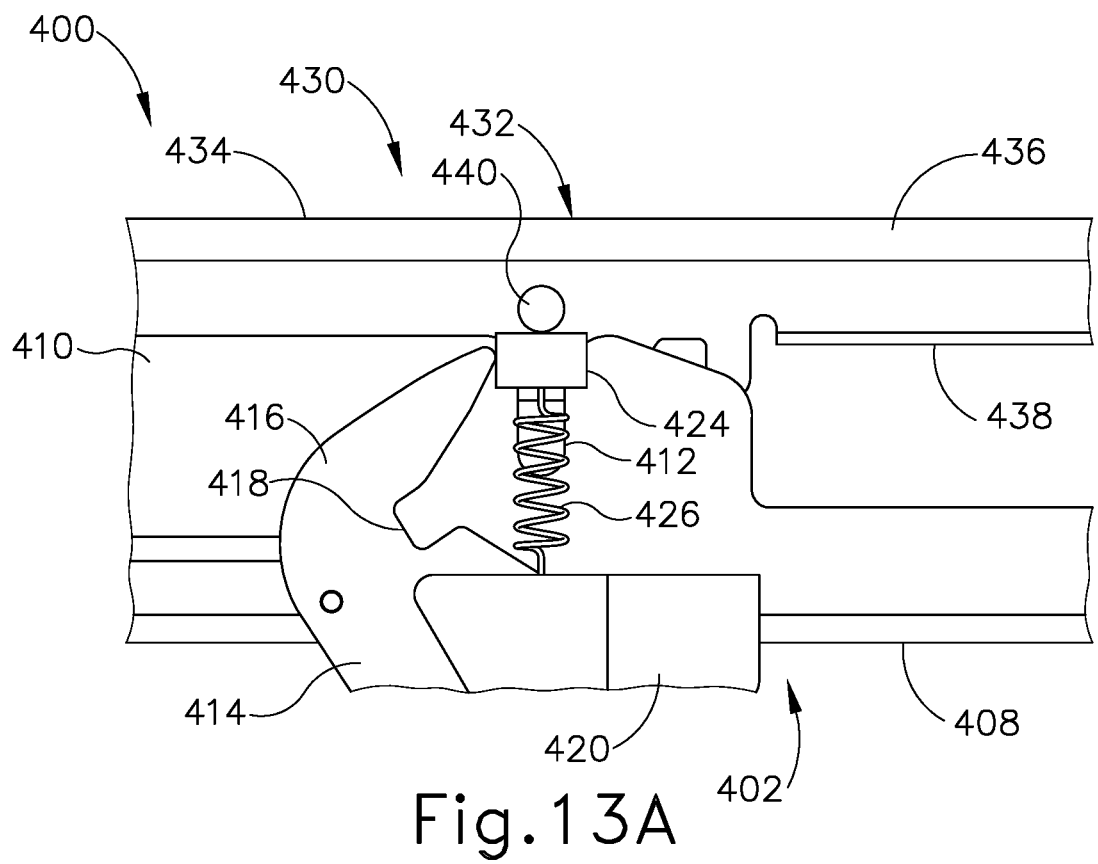
FIG. 13A depicts a side elevational view of the clamping portion of the linear surgical stapler of FIG. 12, showing the blocking element in the extended blocking position.
Figure 13B:
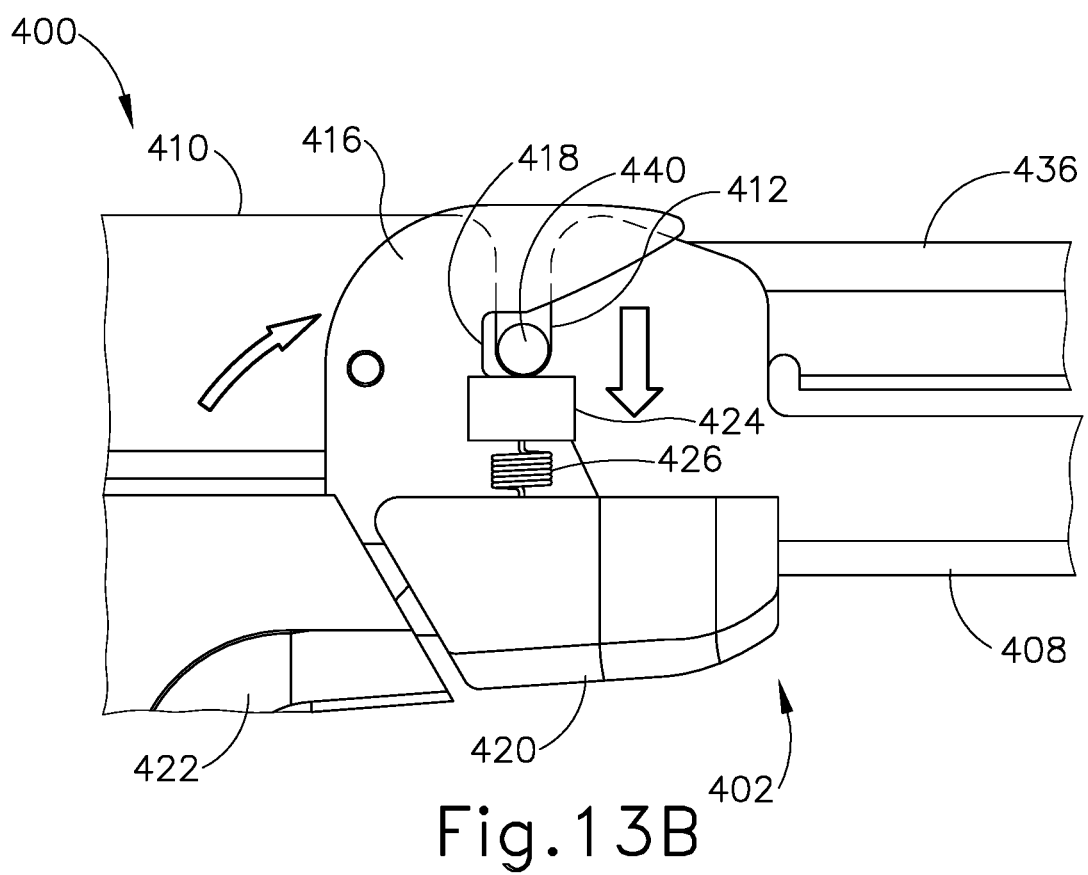
FIG. 13B depicts a side elevational view of the clamping portion of the linear surgical stapler of FIG. 12, showing the blocking element in a retracted position in which the blocking element permits closure of the clamp lever.

C. Exemplary Linear Surgical Stapler Having Closure Lockout Feature on Cartridge Half As described above, each of linear surgical staplers (200, 300) has a clamp lever (260) and a closure lockout feature in the form of lockout pin (250) arranged on anvil half (230, 330). In some instances, however, it may be desirable to locate both the clamp arm and the closure lockout feature of a linear surgical stapler on the cartridge half. FIGS. 12-13B show an exemplary alternative linear surgical stapler (400) having such a configuration. Stapler (400) is similar to staplers (10, 200, 300) described above except as otherwise described below.

As shown in FIG. 12, linear surgical stapler (400) includes a cartridge half (402) and an anvil half (430) configured to releasably couple together to clamp tissue therebetween and simultaneously cut and staple the clamped tissue. Cartridge half (402) includes an elongate cartridge channel (404) having a proximal frame portion (406) configured to slidably house a firing assembly (not shown), and a distal jaw portion (408) configured to receive a staple cartridge (not shown). Proximal frame portion (406) includes a laterally opposed pair of upright side flanges (410) each having a vertical slot (412) arranged at a distal end thereof. A clamp lever (414) is pivotably coupled to a distal end of proximal frame portion (406) and includes a pair of laterally opposed jaws (416) each having a jaw slot (418). In the present version, a first shroud (420) is coupled to an underside of proximal frame portion (434) of cartridge channel (404), and a second shroud (422) is coupled to a proximal arm portion of clamp lever (414).

Cartridge half (402) further includes a closure lockout feature in the form of a block element (424) slidably arranged within one of the vertical slots (412) of cartridge channel (404). A resilient member in the form of a compression spring (426) couples block element (424) to a portion of first shroud (420) and biases block element (424) transversely toward an upper open end of vertical slot (412). As shown in FIGS. 12 and 13A, block element (424) is configured to abut the distal tip of a respective clamp lever jaw (416) and thereby prevent closure of clamp lever (414) when stapler halves (402, 430) are not sufficiently approximated.

As shown in FIGS. 13A-13B, anvil half (430) includes an elongate anvil channel (432) having a proximal frame portion (434) and a distal jaw portion (436) configured to support an anvil surface (438) having a plurality of staple-forming pockets (not shown), which may be similar to staple-forming pockets (238) of anvil surface (240) described above. Anvil half (430) further includes a pin (440) extending laterally through a distal end of proximal frame portion (434), and which is configured to be received within vertical slots (412) of cartridge channel (404) when cartridge half (402) and anvil half (430) are coupled together.

FIG. 13A shows stapler halves (402, 430) after having been coupled together at their proximal ends and pivoted toward one another about their proximal ends such that the opposed lateral ends of anvil pin (440) engage the upper side of block element (424). As distal jaw portion (436) of anvil half (430) is approximated further toward distal jaw portion (408) of cartridge channel (404), anvil pin (440) urges block element (424) downwardly within vertical slot (412) by compressing compression spring (426). As shown in FIG. 13B, further approximation of stapler halves (402, 430) causes block element (424) to disengage the distal tip of clamp lever jaw (416) and enable clamp lever (414) to pivoted closed such that clamp lever (414) captures the opposed ends of anvil pin (440) within jaw slots (412). Accordingly, block element (424) ensures that clamp lever (414) is permitted to close only once anvil pin (440) is sufficiently aligned with and received within the open ends of cartridge channel slots (412), thereby preventing premature closure of clamp lever (414) that would prevent receipt of anvil pin (440) within vertical slots (412). Upon reopening of clamp lever (414) to release anvil pin (440) from cartridge channel slots (412), compression spring (426) expands to return block element (424) to the raised blocking position shown in FIG. 13A.

Figure 14:
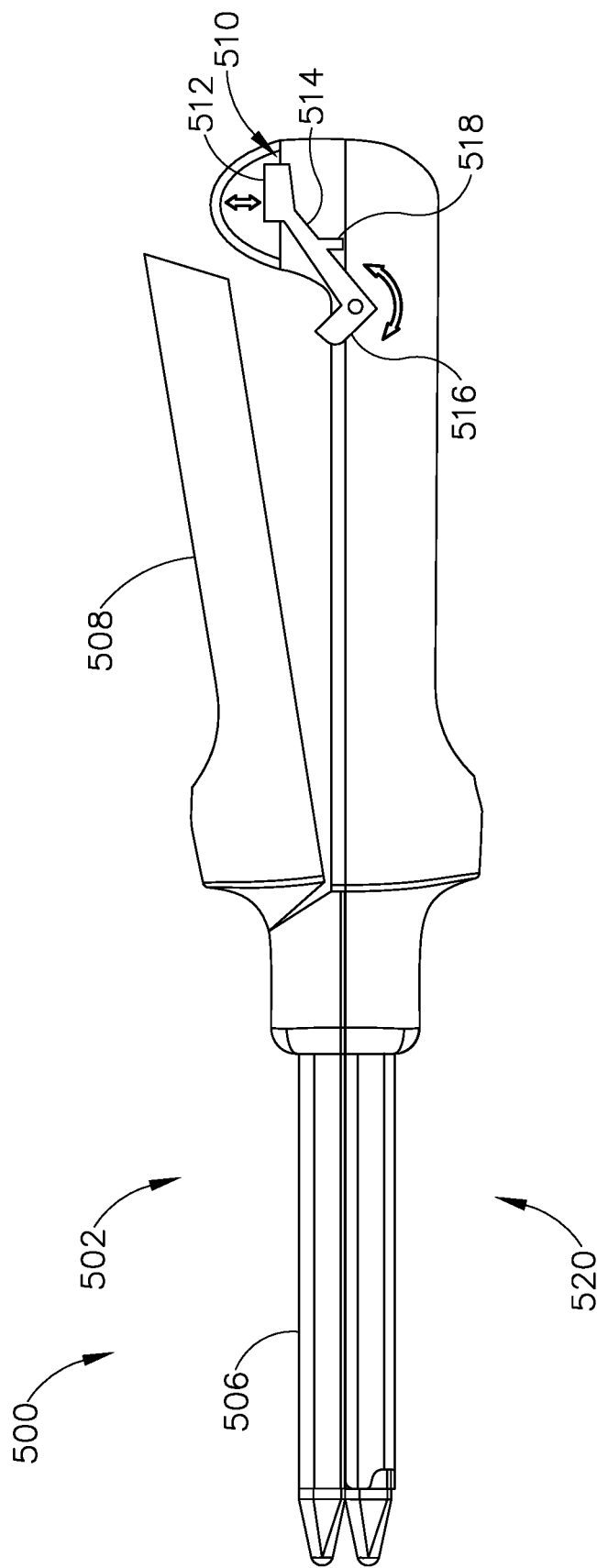
FIG. 14 depicts a schematic side view of another exemplary linear surgical stapler having an assistive element that facilitates opening of the clamp lever for separation of the stapler halves.

III. Exemplary Linear Surgical Stapler Having Assistive Lever for Opening Clamp Lever In some instances, it may be desirable to provide a linear surgical stapler with a feature that assists with the opening of the clamp lever, which may be particular advantageous when the stapler halves are clamped on thicker pieces of tissue with greater clamping forces. FIGS. 14-15B show an exemplary linear surgical stapler (500) having an assistive lever (510) that provides such benefits. Stapler (500) is similar to staplers (10, 200, 300, 400) described above except as otherwise described below.

As shown in FIG. 14, linear surgical stapler (500) includes a cartridge half (502) and an anvil half (520) configured to releasably couple together to clamp tissue therebetween and simultaneously cut and staple the clamped tissue. Cartridge half (502) includes an elongate cartridge channel (504) having a proximal frame portion configured to slidably house a firing assembly that includes an elongate actuating member (504), shown in FIGS. 15A and 15B. A distal jaw portion (506) of cartridge channel (504) is configured to receive a staple cartridge (not shown). Cartridge half (502) further includes a clamp lever (508) pivotably coupled with cartridge channel (504) and configured to pivot between an open position and a closed position to clamp anvil half (520) against cartridge half (502).

Cartridge half (502) further includes an assistive lever (510) pivotably coupled to a proximal portion of cartridge half (502). Assistive lever (510) of the present example includes a proximal head (512), an elongate arm (514) extending distally and angularly downward from head (512), and a distal finger (516) extending angularly upward from a distal end of lever arm (514). As shown in FIG. 14, lever finger (516) is positioned to engage the underside of a proximal end of clamp lever (508). Accordingly, when clamp lever (508) is closed, clamp lever (508) engages distal finger (516) and pivots assistive lever (510) in a first direction such that proximal head (512) rises. When a user wishes to open clamp lever (508), the user depresses proximal head (512), which causes assistive lever (510) to pivot in a second direction and drive distal finger (516) against the underside of the proximal end of clamp lever (508), thereby slightly opening clamp lever (508).

Figure 15A:
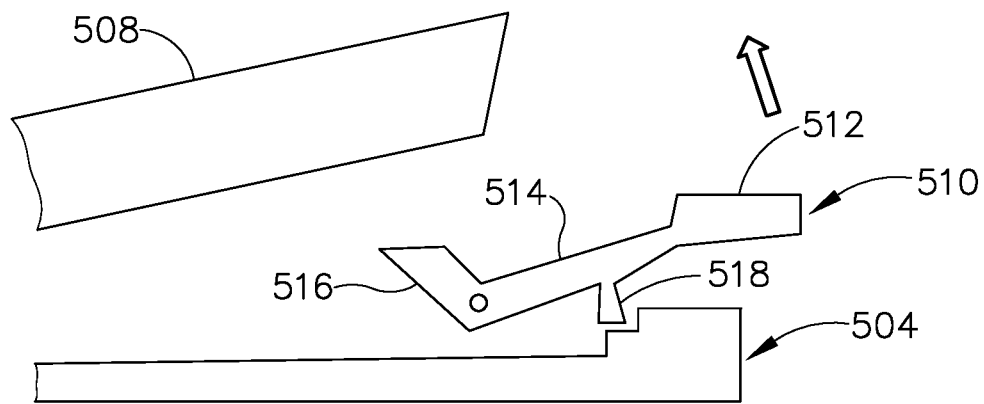
FIG. 15A depicts a schematic side view of the clamp lever, the assistive lever, and a firing assembly member of the linear surgical stapler of FIG. 14, showing the assistive lever in a first rotational position when the clamp lever is open such that a lockout feature of the assistive lever prevents distal translation of the firing assembly member.
Figure 15B:
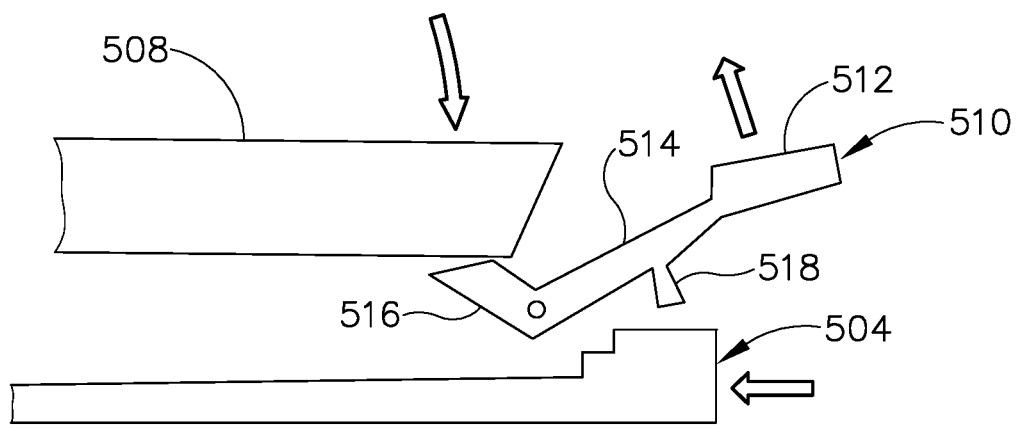
FIG. 15B depicts a schematic side view of the clamp lever, the assistive lever, and the firing assembly member of the linear surgical stapler of FIG. 14, showing the assistive lever in a second rotational position when the clamp lever is closed such that the lockout feature of the assistive lever permits distal translation of the firing assembly member.

As shown in FIGS. 15A and 15B, assistive lever (510) of the present example further includes a firing lockout tab (518) extending downwardly from lever arm (514). As shown in FIG. 15A, when clamp lever (508) is open assistive lever (510) is configured to assume a pivot position in which lockout tab (518) engages a proximal end of firing assembly actuating member (504), thereby block distal actuation of actuating member (504) such that firing is prevented. As shown in FIG. 15B, when clamp lever (508) is closed, clamp lever (508) engages lever arm (514) and causes assistive lever (510) to pivot such that lockout tab (518) disengages firing assembly actuating member (504) and permits firing of stapler (500).

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical stapler comprising: (a) a first elongate member having a distal portion configured to support one of a staple cartridge or an anvil surface having a plurality of staple-forming pockets; (b) a second elongate member having a distal portion configured to support the other of a staple cartridge or an anvil surface having a plurality of staple-forming pockets; (c) a clamp member, wherein the clamp member is movable from an open position to a closed position to releasably clamp the first and second elongate members together; (d) a clamp lockout feature supported by the first elongate member, wherein the clamp lockout feature is moveable between a lockout position in which the clamp lockout feature is configured to prevent closure of the clamp member, and a release position in which the clamp lockout feature is configured to permit closure of the clamp member; and (e) an actuating feature supported by the second elongate member, wherein the actuating feature is configured to actuate the clamp lockout feature from the lockout position to the release position in response to approximation of the distal portions of the first and second elongate members.

Example 2

The surgical stapler of Example 1, wherein the distal portion of the first elongate member supports an anvil surface having a plurality of staple-forming pockets, wherein the distal portion of the second elongate member is configured to support a staple cartridge, wherein the clamp lockout feature and the actuating feature are located proximal to the anvil surface.

Example 3

The surgical stapler of any of the preceding Examples, wherein the clamp member comprises a clamp lever pivotably coupled to the first elongate member with a coupling element.

Example 4

The surgical stapler of Example 3, wherein the coupling element is configured to translate relative to the first elongate member in response to closure of the clamp lever.

Example 5

The surgical stapler of any of Examples 3 through 4, wherein the second elongate member includes a slot configured to capture the coupling element in response to closure of the clamp lever.

Example 6

The surgical stapler of any of the preceding Examples, wherein the clamp lockout feature is configured to translate along a longitudinal axis of the first elongate member between the lockout position and the release position.

Example 7

The surgical stapler of any of the preceding Examples, wherein the lockout position is oriented distally and the release position is oriented proximally.

Example 8

The surgical stapler of any of the preceding Examples, wherein the clamp lockout feature is resiliently biased toward the lockout position.

Example 9

The surgical stapler of any of the preceding Examples, wherein the clamp lockout feature comprises a pin that extends laterally relative to the first elongate member.

Example 10

The surgical stapler of any of the preceding Examples, wherein the actuating feature comprises a ramp, wherein the ramp is configured to cam the clamp lockout feature longitudinally from the lockout position to the release position in response to approximation of the distal portions of the first and second elongate members

Example 11

The surgical stapler of Example 10, wherein the ramp is defined by a notch formed in the second elongate member.

Example 12

The surgical stapler of any of the preceding Examples, further comprising a link coupled with the clamp member, wherein the clamp lockout feature in the lockout position is configured to engage the link to prevent closure of the clamp member, wherein the clamp lockout feature in the release position is configured to disengage the link to permit closure of the clamp member.

Example 13

The surgical stapler of Example 12, wherein a proximal end of the link is pivotably coupled with the first elongate member, wherein a distal end of the link is pivotably coupled with the clamp member.

Example 14

The surgical stapler of any of Examples 12 through 13, wherein the clamp member comprises a clamp lever pivotably coupled with the first elongate member, wherein the link includes a projection configured to releasably engage a free end of the clamp lever.

Example 15

The surgical stapler of any of Examples 12 through 14, wherein a proximal end of the link is coupled to the first elongate member with a coupling element, wherein the surgical stapler further comprises a movable structure supported by the second elongate member, wherein the moveable structure includes a latch feature configured to releasably capture the coupling element to thereby couple a proximal end of the first elongate member with a proximal end of the second elongate member.

Example 16

A surgical stapler comprising: (a) a first elongate member having a distal portion configured to support one of a staple cartridge or an anvil surface having a plurality of staple-forming pockets; (b) a second elongate member having a distal portion configured to support the other of a staple cartridge or an anvil surface having a plurality of staple-forming pockets; (c) a clamp member coupled to a first portion of the first elongate member, wherein the clamp member is movable from an open position to a closed position to releasably clamp the first and second elongate members together; and (d) a link, wherein a first end of the link is coupled to a second portion of the first elongate member, wherein a second end of the link is coupled to the clamp member, wherein the link is operable to prevent closure of the clamp member when the first elongate member is separated from the second elongate member, wherein the link is operable to permit closure of the clamp member in response to approximation of the distal portions of the first and second elongate members.

Example 17

The surgical stapler of Example 16, wherein the first end of the link is pivotably coupled to the second portion of the first elongate member, wherein the second end of the link is pivotably coupled to the clamp member.

Example 18

The surgical stapler of any of Examples 16 through 17, further comprising a lockout feature movable between a lockout position and a release position, wherein the lockout feature in the lockout position is configured to engage the link to prevent closure of the clamp member, wherein the lockout feature in the release position is configured to disengage the link to permit closure of the clamp member.

Example 19

A surgical stapler comprising: (a) a first stapler half having a distal portion with a plurality of staple-forming pockets; and (b) a second stapler half configured to releasably couple with the first stapler half, wherein the second stapler half comprises: (i) a proximal portion, (ii) a distal portion configured to receive a staple cartridge, (iii) a firing assembly, and (iv) a movable structure supported by the proximal portion, wherein the moveable structure comprises: (A) a latch feature, and (B) a firing lockout feature, wherein the movable structure is movable between a first position in which the latch feature captures a proximal feature of the first stapler half and the firing lockout feature permits actuation of the firing assembly, and a second position in which the latch feature releases the proximal feature and the firing lockout feature prevents actuation of the firing assembly.

Example 20

The surgical stapler of Example 19, further comprising a clamp member movable from an open position to a closed position to releasably clamp the first and second stapler halves together, wherein the movable structure further comprises a structure lockout feature configured to prevent the movable structure from moving to the second position when the clamp member is in the closed position.

V. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more of the teachings, expressions, embodiments, examples, etc. described herein may be combined with any one or more of the teachings, expressions, embodiments, examples, etc. described in U.S. application Ser. No. 15/889,363, entitled "Release Mechanism for Linear Surgical Stapler," filed on Feb. 6, 2018, issued as U.S. Pat. No. 10,631,866 on Apr. 28, 2020; U.S. application Ser. No. 15/889,370, entitled "Lockout Assembly for Linear Surgical Stapler," filed on Feb. 6, 2018, issued as U.S. Pat. No. 10.667,818 on Jun. 2, 2020; U.S. application Ser. No. 15/889,374, entitled "Features to Align and Close Linear Surgical Stapler," filed on Feb. 6, 2018, published as U.S. Pub. No. 2019/0239886 on Aug. 8, 2019; U.S. application Ser. No. 15/889,376, entitled "Releasable Coupling Features for Proximal Portions of Linear Surgical Stapler," filed on Feb. 6, 2018, published as U.S. Pub. No. 2019/0239883 on Aug. 8, 2019; U.S. application Ser. No. 15/889,388, entitled "Firing Lever Assembly for Linear Surgical Stapler," filed on Feb. 6, 2018, published as U.S. Pub. No. 2019/0239884 on Aug. 8, 2019; U.S. application Ser. No. 15/889,390, entitled "Clamping Mechanism for Linear Surgical Stapler," filed on Feb. 6, 2018, issued as U.S. Pat. NO. 10,687,819 on Jun. 23, 2020; U.S. application Ser. No. 16/102,164, entitled "Firing System for Linear Surgical Stapler," filed on Aug. 13, 2018, published as U.S. Pub. No. 2020/0046350 on Feb. 13, 2020; U.S. application Ser. No. 16/102,170, entitled "Clamping Assembly for Linear Surgical Stapler," filed on Aug. 13, 2018, published as U.S. Pub. No. 2020/0046353 on Feb. 13, 2020; and U.S. Application Ser. No. 16/157,599, entitled "Anvil Assembly for Linear Surgical Stapler," filed on Oct. 11, 2018, published as U.S. Pub. No. 2020/0113561 on Apr. 16, 2020. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pat. No. 8,844,789, entitled "Automated End Effector Component Reloading System for Use with a Robotic System," issued Sep. 30, 2014, the disclosure of which is incorporated by reference herein; U.S. Pat. No. 8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical stapler comprising:
   (a) a first elongate member having a distal portion configured to support one of a staple cartridge or an anvil surface having a plurality of staple-forming pockets;
   (b) a second elongate member having a distal portion configured to support the other of a staple cartridge or an anvil surface having a plurality of staple-forming pockets;
   (c) a clamp member, wherein the clamp member is movable from an open position to a closed position to releasably clamp the first and second elongate members together;
   (d) a clamp lockout feature supported by the first elongate member, wherein the clamp lockout feature is moveable between a lockout position in which the clamp lockout feature is configured to prevent closure of the clamp member, and a release position in which the clamp lockout feature is configured to permit closure of the clamp member; and
   (e) an actuating feature supported by the second elongate member, wherein the actuating feature is configured to actuate the clamp lockout feature from the lockout position to the release position in response to approximation of the distal portions of the first and second elongate members.

2. The surgical stapler of claim 1, wherein the distal portion of the first elongate member supports an anvil surface having a plurality of staple-forming pockets, wherein the distal portion of the second elongate member is configured to support a staple cartridge, wherein the clamp lockout feature and the actuating feature are located proximal to the anvil surface.

3. The surgical stapler of claim 1, wherein the clamp member comprises a clamp lever pivotably coupled to the first elongate member with a coupling element.

4. The surgical stapler of claim 3, wherein the coupling element is configured to translate relative to the first elongate member in response to closure of the clamp lever.

5. The surgical stapler of claim 4, wherein the second elongate member includes a slot configured to capture the coupling element in response to closure of the clamp lever.

6. The surgical stapler of claim 1, wherein the clamp lockout feature is configured to translate along a longitudinal axis of the first elongate member between the lockout position and the release position.

7. The surgical stapler of claim 6, wherein the lockout position is oriented distally and the release position is oriented proximally.

8. The surgical stapler of claim 1, wherein the clamp lockout feature is resiliently biased toward the lockout position.

9. The surgical stapler of claim 1, wherein the clamp lockout feature comprises a pin that extends laterally relative to the first elongate member.

10. The surgical stapler of claim 1, wherein the actuating feature comprises a ramp, wherein the ramp is configured to cam the clamp lockout feature longitudinally from the lockout position to the release position in response to approximation of the distal portions of the first and second elongate members.

11. The surgical stapler of claim 10, wherein the ramp is defined by a notch formed in the second elongate member.

12. The surgical stapler of claim 1, further comprising a link coupled with the clamp member, wherein the clamp lockout feature in the lockout position is configured to engage the link to prevent closure of the clamp member, wherein the clamp lockout feature in the release position is configured to disengage the link to permit closure of the clamp member.

13. The surgical stapler of claim 12, wherein a proximal end of the link is pivotably coupled with the first elongate member, wherein a distal end of the link is pivotably coupled with the clamp member.

14. The surgical stapler of claim 12, wherein the clamp member comprises a clamp lever pivotably coupled with the first elongate member, wherein the link includes a projection configured to releasably engage a free end of the clamp lever.

15. The surgical stapler of claim 12, wherein a proximal end of the link is coupled to the first elongate member with a coupling element, wherein the surgical stapler further comprises a movable structure supported by the second elongate member, wherein the moveable structure includes a latch feature configured to releasably capture the coupling element to thereby couple a proximal end of the first elongate member with a proximal end of the second elongate member.

16. A surgical stapler comprising:
(a) a first elongate member having a distal portion configured to support one of a staple cartridge or an anvil surface having a plurality of staple-forming pockets;
(b) a second elongate member having a distal portion configured to support the other of a staple cartridge or an anvil surface having a plurality of staple-forming pockets;
(c) a clamp member coupled to a first portion of the first elongate member, wherein the clamp member is movable from an open position to a closed position to releasably clamp the first and second elongate members together; and
(d) a link, wherein a first end of the link is coupled to a second portion of the first elongate member, wherein a second end of the link is coupled to the clamp member, wherein the link is operable to prevent closure of the clamp member when the first elongate member is separated from the second elongate member, wherein the link is operable to permit closure of the clamp member in response to approximation of the distal portions of the first and second elongate members.

17. The surgical stapler of claim 16, wherein the first end of the link is pivotably coupled to the second portion of the first elongate member, wherein the second end of the link is pivotably coupled to the clamp member.

18. The surgical stapler of claim 16, further comprising a lockout feature movable between a lockout position and a release position, wherein the lockout feature in the lockout position is configured to engage the link to prevent closure of the clamp member, wherein the lockout feature in the release position is configured to disengage the link to permit closure of the clamp member.

19. A surgical stapler comprising:
(a) a first stapler half having a distal portion with a plurality of staple-forming pockets; and
(b) a second stapler half configured to releasably couple with the first stapler half, wherein the second stapler half comprises:
  (i) a proximal portion,
  (ii) a distal portion configured to receive a staple cartridge,
  (iii) a firing assembly, and
  (iv) a movable structure supported by the proximal portion, wherein the moveable structure comprises:
    (A) a latch feature, and
    (B) a firing lockout feature,
  wherein the movable structure is movable between a first position in which the latch feature captures a proximal feature of the first stapler half and the firing lockout feature permits actuation of the firing assembly, and a second position in which the latch feature releases the proximal feature and the firing lockout feature prevents actuation of the firing assembly.

20. The surgical stapler of claim 19, further comprising a clamp member movable from an open position to a closed position to releasably clamp the first and second stapler halves together, wherein the movable structure further comprises a structure lockout feature configured to prevent the movable structure from moving to the second position when the clamp member is in the closed position.

* * * * *